United States Patent [19]
Bradley et al.

[11] Patent Number: 5,919,815
[45] Date of Patent: *Jul. 6, 1999

[54] TAXANE COMPOUNDS AND COMPOSITIONS

[75] Inventors: Matthews O. Bradley, Laytonville, Md.; Victor E. Shashoua, Brookline, Mass.; Charles S. Swindell, Merion; Nigel L. Webb, Bryn Mawr, both of Pa.

[73] Assignee: Neuromedica, Inc., Conshohocken, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/653,951

[22] Filed: May 22, 1996

[51] Int. Cl.$^6$ .................................................. A61K 31/335
[52] U.S. Cl. ........................................... 514/449; 549/510
[58] Field of Search .............................. 549/510; 514/449

[56] References Cited

U.S. PATENT DOCUMENTS

| | | | |
|---|---|---|---|
| 4,346,085 | 8/1982 | Growdon et al. | 424/199 |
| 4,351,831 | 9/1982 | Growdon et al. | 514/78 |
| 4,550,109 | 10/1985 | Folkers et al. | |
| 4,554,272 | 11/1985 | Bock et al. | 514/219 |
| 4,636,494 | 1/1987 | Growdon et al. | 514/78 |
| 4,684,646 | 8/1987 | Chang et al. | 514/221 |
| 4,814,470 | 3/1989 | Colin et al. | |
| 4,857,653 | 8/1989 | Colin et al. | |
| 4,933,324 | 6/1990 | Shashoua | 514/549 |
| 4,939,174 | 7/1990 | Shashoua | 514/549 |
| 4,968,672 | 11/1990 | Jacobson et al. | 514/46 |
| 5,116,624 | 5/1992 | Horrobin | 424/702 |
| 5,120,760 | 6/1992 | Horrobin | 514/458 |
| 5,141,958 | 8/1992 | Crozier-Willi et al. | 514/558 |
| 5,194,654 | 3/1993 | Hostetler et al. | |
| 5,216,023 | 6/1993 | Literati et al. | 514/538 |
| 5,223,263 | 6/1993 | Hostetler et al. | |
| 5,246,726 | 9/1993 | Horrobin et al. | 424/646 |
| 5,250,722 | 10/1993 | Bombardelli et al. | |
| 5,336,684 | 8/1994 | Murray et al. | |
| 5,356,928 | 10/1994 | Murray et al. | |
| 5,362,831 | 11/1994 | Mongelli et al. | |
| 5,411,947 | 5/1995 | Hostetler et al. | |
| 5,447,936 | 9/1995 | Hausheer et al. | |
| 5,453,520 | 9/1995 | Bombardelli et al. | |
| 5,453,521 | 9/1995 | Gaullier et al. | |
| 5,468,754 | 11/1995 | Hausheer et al. | |
| 5,473,055 | 12/1995 | Mongelli et al. | |
| 5,476,954 | 12/1995 | Bourzat et al. | |
| 5,484,809 | 1/1996 | Hostetler et al. | |
| 5,516,800 | 5/1996 | Horrobin et al. | 514/560 |
| 5,580,556 | 12/1996 | Horrobin | 424/85.4 |
| 5,580,899 | 12/1996 | Mayhew et al. | 514/449 |

FOREIGN PATENT DOCUMENTS

| | | |
|---|---|---|
| 30009 | 6/1981 | European Pat. Off. |
| 91694 | 10/1983 | European Pat. Off. |
| 59-025327 | 2/1984 | Japan . |
| 1153629 | 6/1989 | Japan . |
| 1203331 | 8/1989 | Japan . |
| 1287022 | 11/1989 | Japan . |
| 6016548 | 1/1994 | Japan . |
| 8027010 | 1/1996 | Japan . |
| 8163991 | 6/1996 | Japan . |
| 9025231 | 1/1997 | Japan . |
| 9603433 | 10/1996 | South Africa . |
| PCT8500520 | 2/1985 | WIPO . |
| WO 89/07938 | 2/1989 | WIPO . |
| WO 94/07880 | 4/1994 | WIPO . |
| WO 94/11547 | 5/1994 | WIPO . |
| WO 94/13654 | 6/1994 | WIPO . |
| WO 9412530 | 6/1994 | WIPO . |
| WO 94/24107 | 10/1994 | WIPO . |
| WO 95/01969 | 1/1995 | WIPO . |
| WO 95/13270 | 5/1995 | WIPO . |
| WO 95/13271 | 5/1995 | WIPO . |
| WO 95/33736 | 12/1995 | WIPO . |
| WO 96/01259 | 1/1996 | WIPO . |

OTHER PUBLICATIONS

Anel, B., et al. "Cytotoxicity of Chlorambucil and Chlorambucil–Fatty Acid Conjugates Against Normal Human Peripheral Blood Lymphocytes", *Biochem Pharmacol*, (1990),40(6):1193–1200. (Abstract).

Oshima, M., et al., "Effects of Docosahexaenoic Acid (DHA) on Intestinal Polyp Development in APC Delta 716 Knockout Mice", *Carcinogenesis*, (1995), 16(11):2605–2607. (Abstract).

Deutsch, H.F., et al., "Cytotoxic Effects of Daunomycin–Fatty Acid Complexes on Rat Hepatoma", *Cancer Res*, (1983), 43(6):2668–2672. (Abstract).

Karmali, R.A., et al., "Effect of Omega–3 Fatty Acids on Growth of a Rat Mammary Tumor", *J Natl Cancer Inst* (1984), 73(2):457–461. (Abstract).

Tinsley, I.J., et al., "Influence of Dietary Fatty Acids on the Incidence of Mammary Tumors in the CH3H Mouse", *Cancer Res*, (1981), 41(4):1460–1465. (Abstract).

Anel, A., et al., "Increased Cytotoxicity of Polyunsaturated Fatty Acids on Human Tumoral B and T–Cell Lines Compared with Normal Lymphocytes", *Leukemia*, (1992), 6(7):680–688. (Abstract).

Jenski, L.J., et al., "Docosahexaenoic Acid–Induced Alteration of THY–1 and CD8 Expression on Murine Splenocytes", *Biochim Biophys Acta*, (1995), 1236(1):39–50. (Abstract).

de Antueno, R.J., et al., "In Vitro Effect of Eicosapentaenoic and Docosahexaenoic Acids on Prostaglandin E2 Synthesis in a Human Lung Carcinoma", *Biochem Int*, (1989), 19(3):489–496. (Abstract).

Kinsella, J.E., et al., "Effects of Polyunsaturated Fatty Acids on the Efficacy of Antineoplastic Agents Toward L5178Y Lymphoma Cells", *Biochem Pharmacol*, (1993), 45(9):1881–1887. (Abstract).

(List continued on next page.)

*Primary Examiner*—James H. Reamer
*Attorney, Agent, or Firm*—Wolf, Greenfield & Sacks, P.C.

[57] ABSTRACT

The invention provides taxanes that are conjugates of cis-docosahexaenoic acid and paclitaxel. The conjugates are useful in treating cancer.

8 Claims, 14 Drawing Sheets

OTHER PUBLICATIONS

Ehringer, W., et al., "A Comparison of the Effects of Linolenic (18:3 Omega 3) and Docosahexaenoic (22:6 Omega 3) Acids on Phospholipid Bilayers", *Chem Phys Lipids,* (1990), 54(2):79–88. (Abstract).

Guffy, M.M., et al., "Effect of Cellular Fatty Acid Alteration on Adriamycin Sensitivity in Cultured L1210 Murine Leukemia Cells", *Cancer Res,* (1984), 44(5):1863–1866. (Abstract).

Madhavi, N., et al., "Effect of N–6 and N–3 Fatty Acids on the Survival of Vincristine Sensitive and Resistant Human Cervical Carcinoma Cells In Vitro", *Cancer Lett,* (1994), 84(1):31–41. (Abstract).

Kinsella, J.E., et al., "Effects of Polyunsaturated Fatty Acids on the Efficacy of Antineoplastic Agents Toward L5178Y Lymphoma Cells", *Biochem Pharmacol,* (1993,) 45(9):1881–1887. (Abstract).

Begin, M.E., et al., "Differential Killing of Human Carcinoma Cells Supplemented with N–3 and N–6 Polyunsaturated Fatty Acids", *J Natl Cancer Inst,* (1986), 77(5):1053–1062. (Abstract).

Falconer, J.S., et al., "Effect of Eicosapentaenoic Acid and Other Fatty Acids on the Growth In Vitro of Human Pancreatic Cancer Cell Lines", *Br J Cancer,* (1994,) 69(5):826–832. (Abstract).

Plumb, J.A., et al., "Effect of Polyunsaturated Fatty Acids on the Drug Sensitivity of Human Tumour Cell Lines Resistant to Either Cisplatin or Doxorubicin", *Br J Cancer,* (1993), 67(4):728–733. (Abstract).

de Smidt, P.C., et al., "Characteristics of Association of Oleoyl Derivatives of 5–Fluorodeoxy–Uridine and Methotrexate with Low–Density Lipoproteins (LDL)", *Pharm Res,* (1992), 9(4):565–569. (Abstract).

Zijlistra, J.G., et al., "Influence of Docosahexaenoic Acid In Vitro on Intracellular Adriamycin Concentration in Lymphocytes and Human Adriamycin–Sensitive and Resistant Small–Cell Lung Cancer Cell Lines, and on Cytotoxicity in the Tumor Cell Lines", *Int J Cancer,* (1987), 40(6):850–856. (Abstract).

Karmali, R., "N–3 Fatty Acids: Biochemical Actions in Cancer", *J Nutr Sci Vitaminol* (Tokyo), (1992), 148–152. (Abstract).

Chajes, V., et al., "Influence on N–3 Fatty Acids on the Growth of Human Breast Cancer Cells In Vitro: Relationship to Peroxides and Vitamin–E", *Breast Cancer Res Treat,* (1995), 34(3):199–212. (Abstract).

Minami, M., et al., "Effects of Low–Dose Eicosapentaenoic Acid, Docosahexaenoic Acid and Dietary Fat on the Incidence, Growth and Cell Kinetics of Mammary Carcinomas in Rats", *Oncology,* (1996), 53(5):398–405. (Abstract).

Burns, C.P., et al., "Effect of Docosahexaenoic Acid on Rate of Differentiation of HL–60 Human Leukemia", *Cancer Res,* (1989), 49(12):3252–3258. (Abstract).

Pascale, A.W., et al., "Omega–3 Fatty Acid Modification of Membrane Structure and Function. Alteration by Docosahexaenoic Acid of Tumor Cell Sensitivity to Immune Cytolysis", *Nutr Cancer,* (1993), 19(2):147–157. (Abstract).

Zerouga, M., et al., "Phospholipid Class as a Determinant in Docosahexaenoic Acid's Effect on Tumor Cell Viability", *Anticancer Res,* (1996), 16(5A):2863–2868. (Abstract).

Jenski, L.J., et al., "Omega–3 Fatty Acid–Containing Liposomes in Cancer Therapy", *Proc Soc Exp Biol Med,* (1995), 210(3):227–233. (Abstract).

Jenski, L.J., et al., "Omega 3 Fatty Acids Increase Spontaneous Release of Cytosolic Components From Tumor Cells", *Lipids,* (1991), 26(5):353–358. (Abstract).

Tessier, C., et al., "Docosahexaenoic Acid is a Potent Inhibitor of Rat Uterine Stromal Cell Proliferation", *Biochem Biophys Res Commun,* (1995), 207(3):1015–1021. (Abstract).

C.S. Swindell et al., "Characterization of the Taxol Structure–Activity Profile for the Locus of the A–Ring Side Chain", *Bioorganic & Medicinal Chem. Ltrs.,* vol.4, No. 12, pp. 1531–1536 (1994).

J.M. Carboni et al., "Synthesis of a Photoaffinity Analog of Taxol as an Approach to Identify the Taxol Binding Site on Microtubules", *Journal of Medicinal Chem.* (Sep. 8, 1992).

K.C. Nicolaou et al., "Design, Synthesis and Biological Activity of Protaxols", *Nature,* 364: 464–466 (Jul 29, 1993).

G.I. Georg et al., "The Medicinal Chemistry of Taxol", in "Taxol Science and Applications" ed. Matthew Suffness. Boca Raton: CRC Press, Inc., 1995, pp. 317–375.

W.C. Rose, Preclinical Antitumor Activity of Taxanes, in "Taxol Science and Applications" ed. Matthew Suffness. Boca Raton: CRC Press, Inc., 1995, pp. 317–375.

T. Higuchi et al., "Prodrugs as Novel Drug Delivery Systems", *American Chem. Society,* ACS Symposium Series, vol. 14, pp. 14–15 (1975).

S. Iwakami et al., "Inhibition of Arachidonate 5–Lipoxygenase by Phenolic Compounds", *Chem. Pharm. Bull.* (Japan), 34 (9), 3960–3963, 1986.

Y. Makino et al., Chemical Abstracts, vol. 106, No. 12, issue Mar. 23, 1987, "Pharmaceuticals Permeable to Blood–Brain Barrier", p. 363, dated Sep. 10, 1986.

Hesse, G.W. et al., "Uptake in brain and neurophysiological activity of two lipid esters of gamma–aminobutyric acid", *Neuropharamacol.* 27:637–40 (1988).

Jacob, J.N. et al., "Gamma–aminobutyric acid esters, 3, Synthesis, brain uptake, and pharmacological properties of C–18 Glyceryl lipid esters of GABA with varying degree of unsaturation", *Journal of Medicinal Chem.* 30:1573–6 (1987).

Jacob, J.N. et al., "Synthesis, brain uptake and pharmacological properties of a glyceryl lipid containing GABA and the GAB–T inhibitor, gamma–vinyl–GABA", *J. Medicinal Chem.* 33:733–6 (1990).

Ferrari et al., 9–cis–6,6'–diapo–gamma, gamma–carotenedioic acid derivatives and pharmaceutical compositions containing them. p. 710. Abs. 20423w. Chem. Abs. 95(23), Dec. 7, 1981.EP30.009 Jun. 10, 1981.

G. Dhopeshwarker, Chemical Abstracts, vol. 76, No. 16, issued Apr. 17, 1972, "Fatty Acid Transport Into the Brain", p. 276, Abstract No. 97635c, Biochim Biophys. Acta 1972, 255(2) 572–9.

R. Spector, Chemical Abstracts, vol. 108, No. 11, issued Mar. 14, 1988, "Fatty Acid Transport Through the Blood––Brain Barrier", p. 435, Abstract No. 92100g, J. Neurochem., 1988, 50(2). 639–43.

I. Yamatsu et al., Chemical Abstracts, vol. 100, No. 19, issued May 7, 1984, "Polyprenyl Carboxylic Acid Amides", p. 555, Abstract No. 156839z, EP91,694 dated Oct. 19, 1983.

V.E. Shashoua, et al., "Gamma–Aminobutyric Acid Esters,1, Synthesis . . .", *Journal of Medicinal Chemistry,* vol. 27, No. 5, pp. 659–664 (1984).

G. Bourat et al., "Long Chain Esters of Pipotiazine as Long–Acting Psychotropic Pro–Drugs", pp. 105–114, (1976) Med. Chem. Proc. Int. Sym. 5.

K.A. Jacobson et al., "Adenosine analogs with covalently attached lipids . . . ", *FEBS Letters,* vol. 225, Nos. 1,2 pp. 97–102 (Dec. 1987).

A. Garzon–Aburbeh et al., "A Lymphotrophic Prodrug of L–Dopa:Synthesis", *Journal of Medicinal Chemistry,* 29: 687–691 (1986).

J.N. Jacob, et al., "Gamma–Aminobutyric Acid Esters,2, Synthesis Brain Uptake . . . ", *Journal of Medicinal Chem.,* Vo. 28, No. 1, pp. 106–110 (1985).

G.W. Hesse et al., "Inhibitory Effect of Cholesterol Gamma–Aminobutyrate", *Neuropharmacology,* vol. 24, No. 2, pp. 139–146 (1985).

U.K. Mazumdar & D.C. Dev. "Preparation and Evaluation of Ethambutol Derivatives", Indian J. Pharm. Sci. 47(6):179–180 (1984).

L.M. Gunne et al., "Oral Dyskinesia in Rats Following Brain Lesions and Neuroleptic Drug Administration", Psychopharmacology 77:134–9 1982.

R.J. Baldessarnini et al., "Dopamine and the Pathophysiology of Dyskinesis . . . ", *Ann. Rev. Neurosci.,* 3: 23–41 (1980).

J.P. Lohr et al., "Neuroleptic–Induced Movement Disorders . . . ", *Psychiatry* vol. 3 (1989).

TAXANE COMPOUNDS AND COMPOSITIONS

BACKGROUND OF THE INVENTION

Taxol® (paclitaxel) was first isolated in 1971 from the bark of *Taxus brevifolia* and was approved in 1992 by the U.S. Food and Drug Administration for treatment of metastatic ovarian cancer and later for breast cancer. Its mechanism of action is believed to involve promoting formation and hyperstabilization of microtubules, thereby preventing the disassembly of microtubules necessary for completion of cell division. It also has been reported that Taxol induces expression of cytokines, affects the activity of kinases and blocks processes essential for metastasis, in as yet uncharacterized mechanisms of action.

Taxol has attracted unusually strong scientific attention, not only because of its unique antiproliferative mechanism of action, but also because it is active against nearly all cancers against which it has been tested and because it has been discovered to be an analog of numerous closely related compounds occurring naturally. These compounds, taxanes, are now recognized as a new class of anticancer compounds.

Taxol's strength against cancers of diverse tissue origin also represents a significant drawback. An ideal anticancer agent has tissue specificity, thereby reducing side-effects on normal (dividing) cells. Taxol analogs with tissue specificity therefore are desired. Another drawback of Taxol is its extreme insolubility. Taxol can be administered effectively in a solvent including cremophor, which combination can provoke severe hypersensitive immune responses. As a result of these drawbacks, and also as a result of the potential for modifying Taxol at numerous sites as demonstrated by other naturally-occurring taxanes with anticancer activity, a search for more selective taxanes was launched.

To date, more than 200 taxanes have been synthesized (or isolated) and tested in vitro or in vivo for anticancer activity. The results, however, have been so disappointing that the National Cancer Institute (NCI) generally no longer is interested in testing Taxol analogs. In general with Taxol analogs, the solubility problems remain, and/or potency is sharply reduced, and/or selectivity is not improved, and/or the ratio of the median toxic dose to the median effective dose ("therapeutic index") is unacceptably reduced.

Taxol has the following formula:

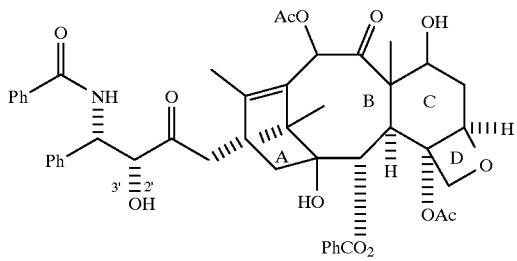

Taxanes have the basic three ring structure (A, B and C), substituted or unsubstituted. Taxol's carbons are numbered conventionally as follows:

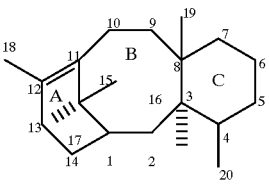

Based upon the taxanes tested to date, as many questions have been raised as have been answered, and general rules have not been fashioned easily in predicting selectivity, activity and solubility. Firstly, no rules have emerged regarding selectivity. Those taxanes that are strongly active appear to have activity as broad as Taxol's activity, and no headway appears to have been made in terms of developing a more selective Taxol analog.

Some information about activity has emerged. Numerous substitutions have been made at C7, C9, C10, C19, $R_1$ and combinations thereof while retaining significant, but usually reduced, activity. Substitutions at C2, C4 and 2'OH, however, are generally not tolerated. These conclusions are only generalities, for example, because some substitutions at C9–C10 (cyclic derivatives) are not tolerated and some substitutions at C2 (meta substitutions on the phenyl) are tolerated. Likewise, the C13 side chain and, in particular, the 2'OH are required, although the minimum structural requirements of the side chain have not been determined for therapeutic efficacy.

Among the most promising of the two hundred analogs tested is Taxotere (N-dibenzoyl-N-tert-(butoxycarbonyl)-10-deacetyltaxol), because of its slightly increased activity and solubility. Oddly, however, Taxotere differs from Taxol at sites which typically do not have a strong influence on activity, and one would not predict the improvements in Taxotere from these differences, even in hindsight.

Attempts to improve Taxol's solubility have not resulted in successful clinical products. One approach has been to manufacture prodrugs of Taxol, which prodrugs undergo in vivo transformation into Taxol and some other product. Attempts were made to esterify the C7 hydroxy and 2'hydroxy groups, with the hope that the bond would be stable in solution (to permit preferred administration modes—i.v. over at least 24 hours) but would cleave readily in vivo. The groups tested were all hydrophilic and included amines, short carboxylic acids (using e.g. succinic anhydride and glutaric anhydride), sulfonic acids, amino acids and phosphates. Generally, activity was reduced although some success was obtained with certain derivatives. Again, no particular pattern emerged permitting one to predict reliably which groups could be substituted on Taxol to yield a therapeutically useful product, although it was suggested that the 2'OH derivatives may cleave more easily than the C7 OH derivatives.

Several other factors add to the problem of predicting which Taxol analogs will be effective. Multiple mechanisms of action have been proposed in the literature, and a change in one position may have no effect on activity on one such mechanism but may eliminate activity on another mechanism. In addition, changes that favorably influence activity may unfavorably influence bioavailability. For example, Taxol affects microtubule formation inside a cell, but a change in structure that increases intracellular activity may adversely affect the ability of Taxol to gain entry into a cell. Taxol also is known to bind to proteins, and the effect on activity that results from a change in Taxol binding to protein (in terms of conformation, cellular absorption and solubility) is unknown.

It has been reported that Taxol does not get into the brain, apparently excluded by the blood brain barrier. It is not known why this is so, as Taxol is lipophilic, gets into cells and might be expected to cross the blood brain barrier.

DHA (docosahexaenoic acid) is a 22 carbon naturally-occurring, unbranched fatty acid that previously has been attached to drugs to help deliver them across the blood brain barrier. DHA is attached via the acid group to hydrophilic drugs and renders these drugs more hydrophobic (lipophilic). DHA is an important constituent of the brain and recently has been approved in Europe as an additive to infant formula. It is present in the milk of lactating women. The mechanism of action by which DHA helps drugs conjugated to it cross the blood brain barrier is unknown.

SUMMARY OF THE INVENTION

The present invention involves the unexpected finding that conjugates of Taxol and a highly lipophilic group, a C22 unbranched carbon chain, have a different selectivity relative to Taxol. The conjugates, in general, render the activity of the taxanes selective for colon cancer, breast cancer, and central nervous system cancer ("targeted cancers"). The conjugates, also unexpectedly, restrict the activity of the taxanes even within these three categories of cancer relative to that of Taxol. The conjugates, further unexpectedly, reduce sharply the activity of the taxane relative to that of Taxol in most cell lines of tissue types other than colon, breast, and central nervous system, thereby reducing potential side effects of the conjugates versus those of Taxol. The therapeutic index of the conjugates is improved, versus that of Taxol for targeted cancers.

According to one aspect of the invention, a composition of matter is provided. The composition is a covalent conjugate of cis-docosahexaenoic acid and paclitaxel. In one embodiment the conjugate is:

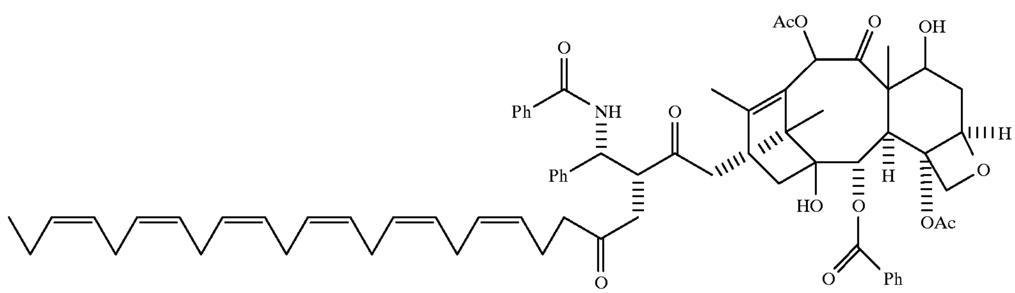

In another embodiment the conjugate is:

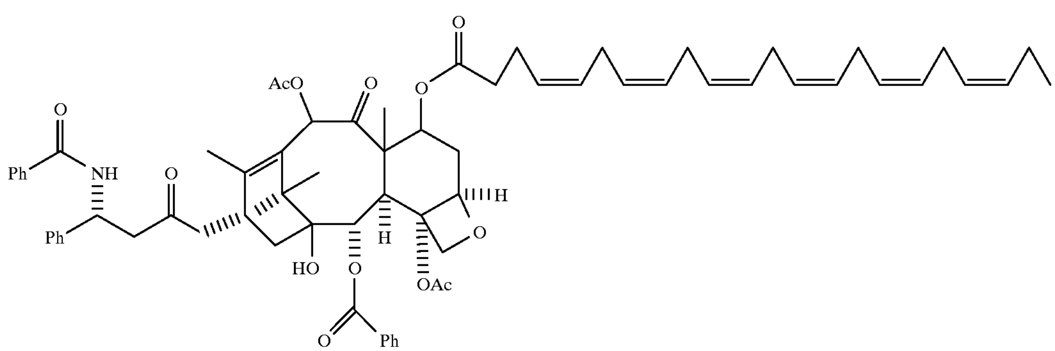

Pharmaceutical preparations containing one or more of the foregoing conjugates also are provided. The pharmaceutical preparations preferably include a sterile, pharmaceutically acceptable carrier. The pharmaceutical preparations also can contain other anti-cancer agents.

The foregoing compositions of matter and pharmaceutical preparations are useful for treating cancer, preferably breast cancer, colon cancer and central nervous system cancer.

Figure 1:
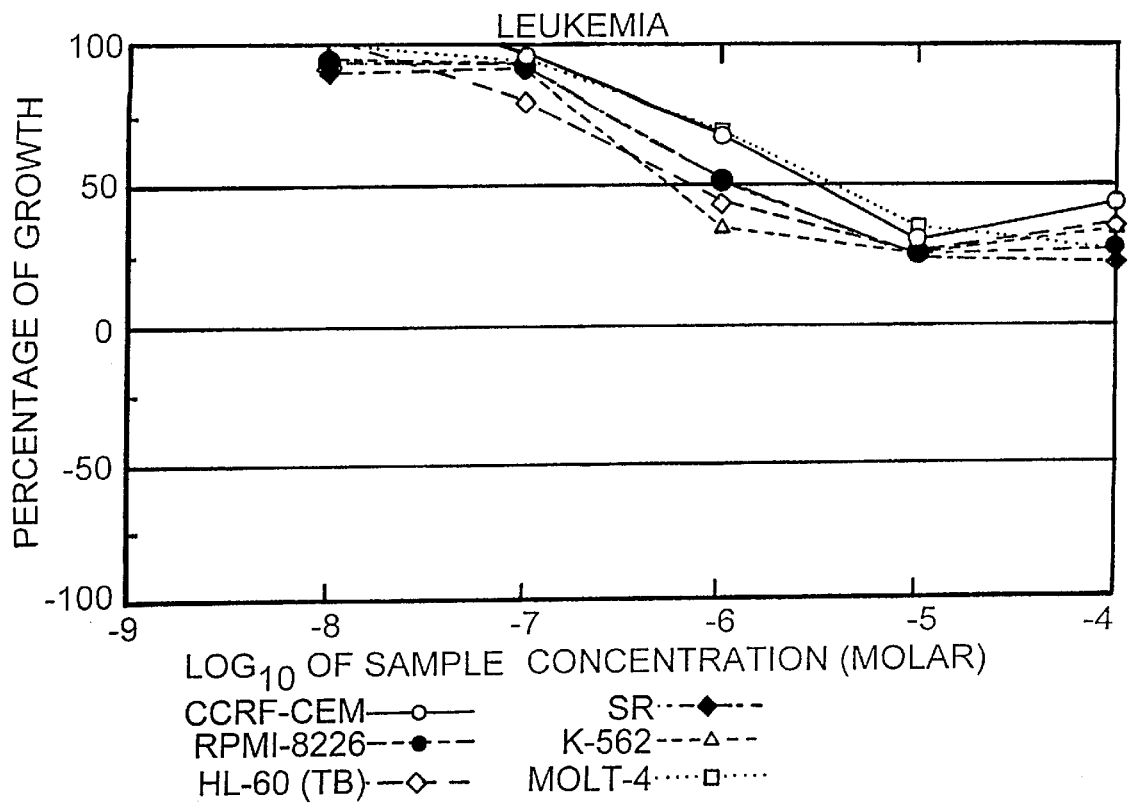
FIG. 1 is a graph plotting concentration of conjugate1 versus percent growth of leukemia cells.

DETAILED DESCRIPTION OF THE INVENTION cis-docosahexaenoic acid (DHA) is a naturally occurring fatty acid. It is an unbranched chain fatty acid with six double bonds, all cis. Its structure is as follows:

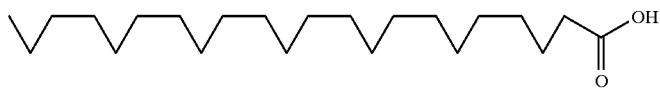

DHA can be isolated, for example, from fish oil or can be chemically synthesized. These methods, however, can generate trans isomers, which are difficult and expensive to separate and which may present safety problems in humans. The preferred method of production is biological synthesis to produce the all cis isomer. The preferred source of DHA is from Martek Biosciences Corporation of Columbia, Md. Martek has a patented system for manufacturing DHA using microalgae which synthesize only a single isomer of DHA, the all cis isomer. Martek's patents include U.S. Pat. Nos. 5,374657, 5,492,938, 5,407,957 and 5,397,591.

DHA also is present in the milk of lactating women, and Martek's licensee has obtained approval in Europe of DHA as a nutritional supplement for infant formula.

DHA can be unstable in the presence of oxygen. To stabilize DHA and its conjugates it is important to add anti-oxidants to the material after it is synthesized. One method of stabilization is to make-up the newly synthesized material in the following solution: 100 g neat DHA-taxol plus 100 g of vehicle (100 ml propylene glycol, 70 mg alpha-tocopherol, 5 mg dilaurylthiodipropionic acid, 50 mg ascorbic acid) prepared and held under argon in amber, sealed vials and stored at four degrees centigrade. The following anti-oxidants may also be employed: ascorbic acid, ascorbyl palmitate, dilauryl ascorbate, hydroquinone, butylated hydroxyanisole, sodium meta bisulfite, t-β carotene and α-tocopherol. A heavy metal chelator such as ethylenediamine tetra-acetic acid (EDTA) may also be used.

Paclitaxel was first isolated from the bark of *Taxus brevifolia* (Wani et al., *J. Am. Chem. Soc.*, 93, 2325, 1971). Its isolation and synthesis have been reported extensively in the literature. Applicants obtained paclitaxel from a commercial source, Hauser Laboratories, of Boulder, Colo.

EXAMPLE 1

TAXOL

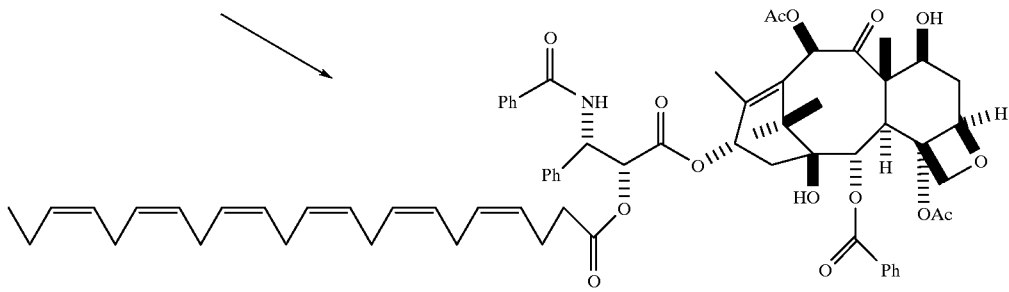

Conjugate 1

Taxol (59 μmol) in dimethylformamide (3 mL) under argon was mixed with 4-dimethylaminopyridine (59 μmol), dicyclohexylcarbodiimide (117 μmol), and DHA (59 μmol). The reaction mixture was stirred at ambient temperatures for ten hours, diluted with ether, washed with water, 5% hydrochloric acid and saturated aqueous sodium chloride, dried with sodium sulfate, and concentrated. Radial chromatography of the residue produced 9 mg (28%) of Taxol-DHA conjugate 1 and 34 mg (68%) of recovered Taxol.

EXAMPLE 2

A second procedure produces a higher yield of conjugate 1. A solution of Taxol (41 μmol) in methylene chloride (2.5 mL) under argon was mixed with 4-dimethylaminopyridine (41 μmol), dicyclohexylcarbodiimide (82 μmol), and DHA (41 μmol) and the reaction mixture was stirred at ambient temperature for two hours. Following dilution with ether, the reaction mixture was washed with 5% hydrochloric acid, water, saturated aqueous sodium chloride, dried, and concentrated. Radial chromatography of the residue produced 45 mg (94%) of crystalline Taxol-DHA conjugate 1.

EXAMPLE 3

TAXOL ⟶ 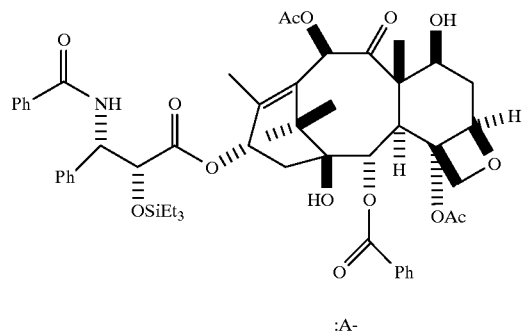

:A-

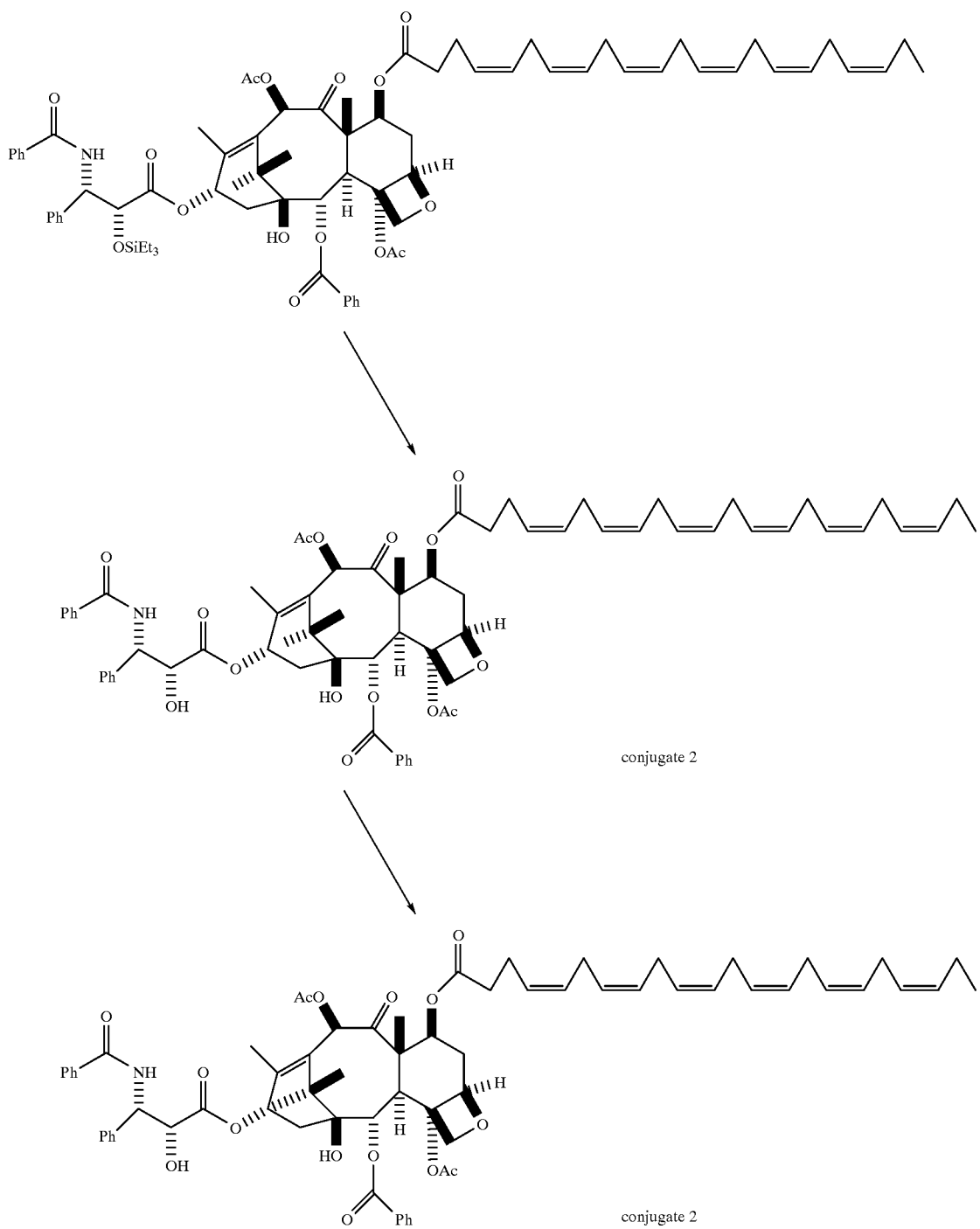

conjugate 2 conjugate 2

The production of conjugate 2 involves several steps including a number of protection-acylation-deprotection steps. A solution of Taxol (59 μmol) in methylene chloride (2.5 mL) was mixed at ambient temperature under argon with imidazole (147 μmol) and triethylsilyl chloride (147 μmol). The reaction mixture was stirred for thirty minutes, diluted with additional methylene chloride, washed with water, saturated aqueous sodium chloride, dried, and concentrated. Chromatography of the residue produced 50 mg (88%) of intermediate A plus 5 mg of the 2',7-di (triethylsilyl) ether derivative. A solution of intermediate A (52 μmol) in methylene chloride (3 mL) was mixed at ambient temperature under argon with 4-dimethylaminopyridine (52 μmol), dicyclohexylcarbodiimide (104 μmol), and DHA (52 μmol). The reaction mixture was stirred for ten hours, diluted with ether, passed through celite, and concentrated. Chromatography of the residue produced 65.9 mg of intermediate B. A solution of intermediate B (51 μmol) in acetonitrile (2 mL) at 0° C. under argon was mixed with 49% aqueous HF (0.2 mL) and the reaction mixture was stirred for one hour. After dilution with ether, the reaction mixture was washed with water, saturated aqueous sodium chloride, dried, and concentrated. Radial chromatography of the residue produced 44.6 mg (75%) of Taxol-DHA conjugate 2.

EXAMPLE 4

Conjugates 1 and 2 were sent to the United States National Cancer Institute (NCI) for screening in the NCI's anticancer screening program. The conjugates were provided in ethanol (approximately 40 mg analog/2 ml ethanol). The conjugates were sealed in vials under argon to avoid exposure of the conjugates to oxygen because the conjugates are believed to be sensitive to oxygen. Instructions were provided to store at 4° C. and to open the vials only when ready for immediate experimental use. Instructions also were provided to use the ethanol solutions containing the conjugates directly or to dissolve the conjugates further in DMSO (dimethylsulfoxide) at appropriate concentrations, with vortexing if necessary for adequate dispersal.

Figure 2:
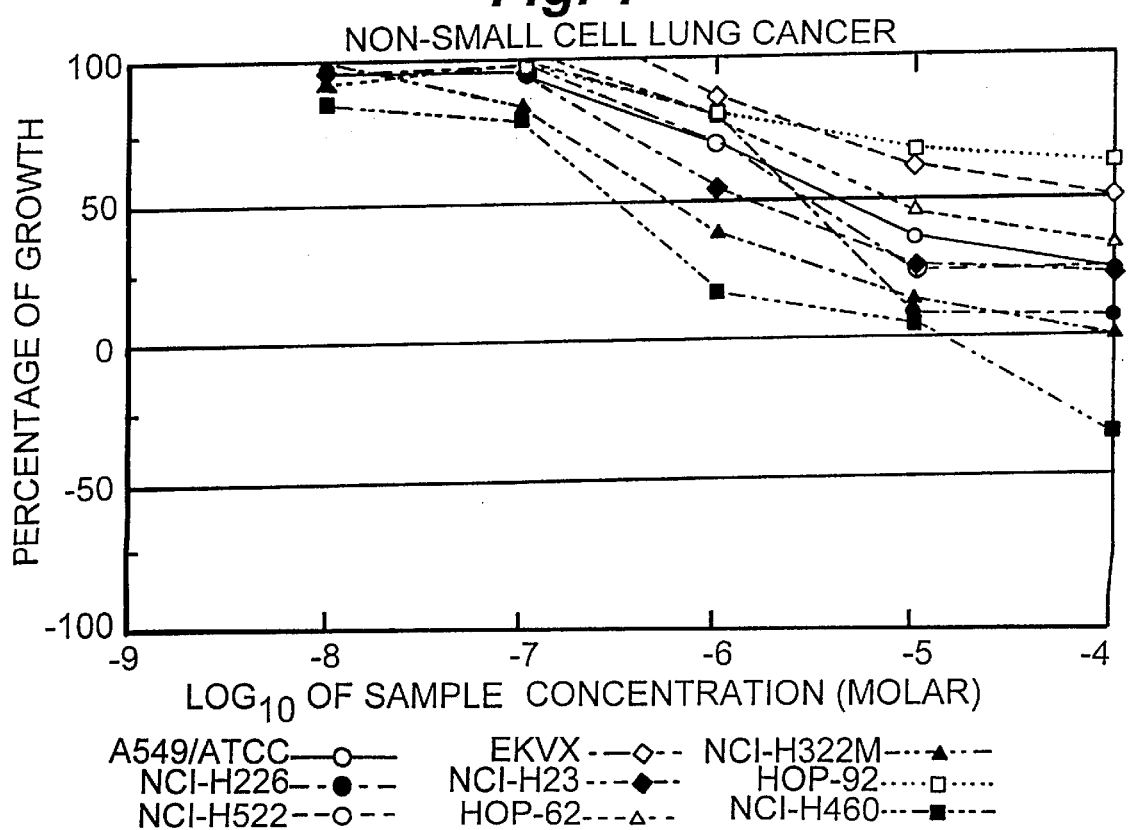
FIG. 2 is a graph plotting concentration of conjugate 1 versus percent growth of non-small cell lung cancer cells.
Figure 3:
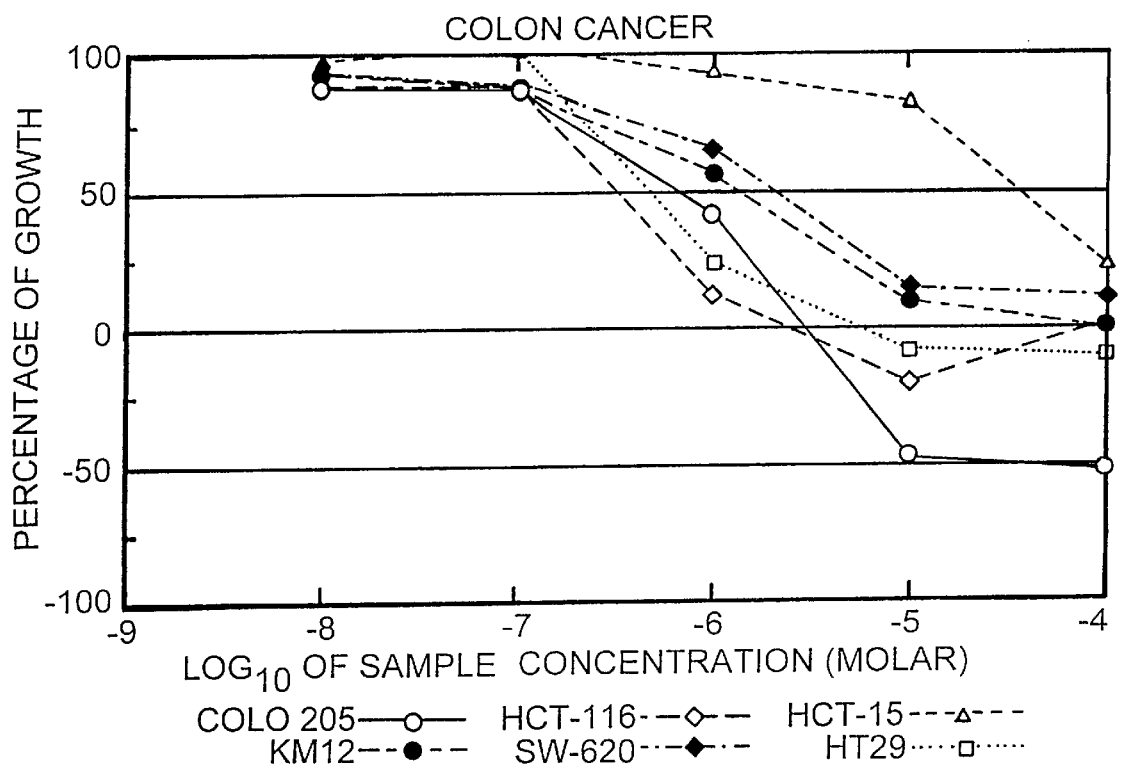
FIG. 3 is a graph plotting concentration of conjugate 1 versus percent growth of colon cancer cells.
Figure 4:
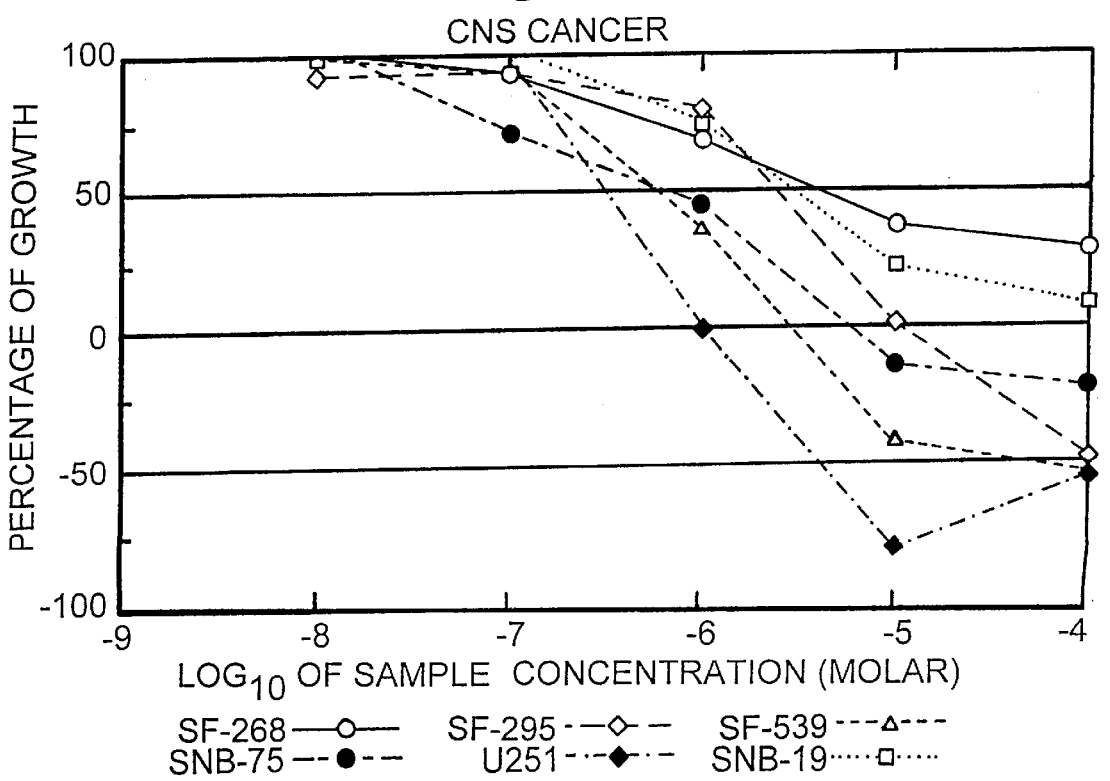
FIG. 4 is a graph plotting concentration of conjugate 1 versus percent growth of CNS cancer cells.
Figure 5:
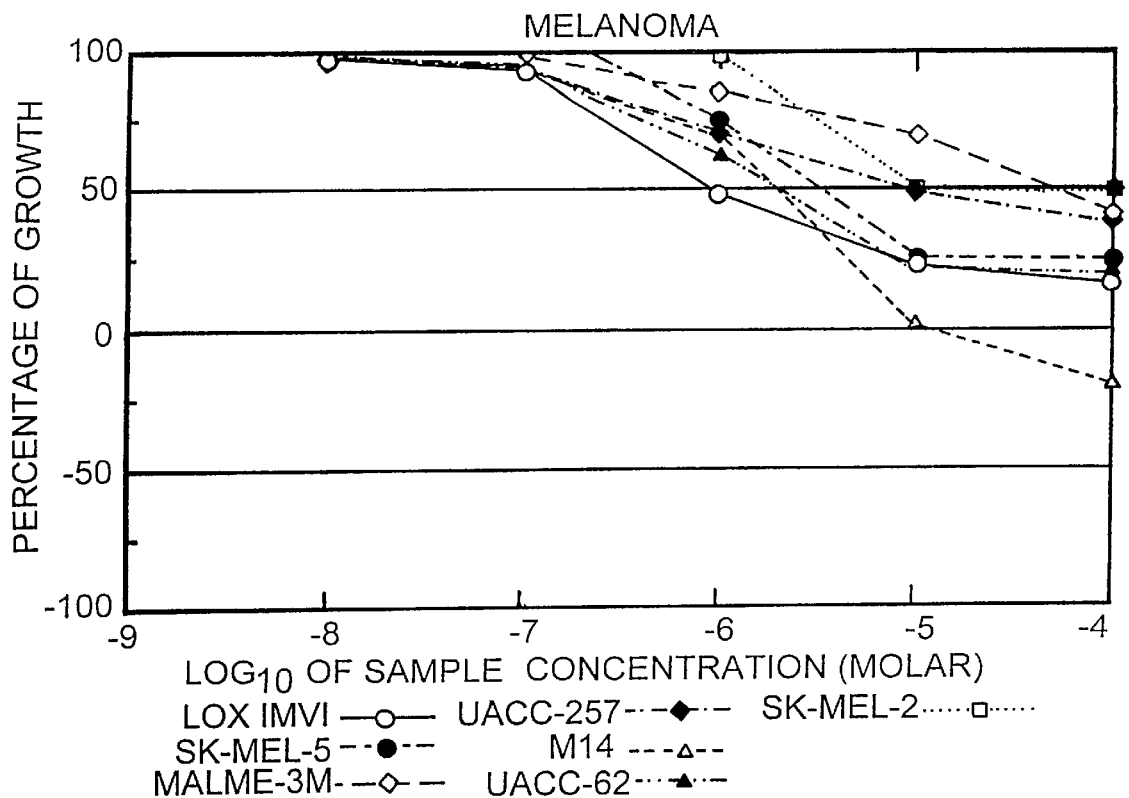
FIG. 5 is a graph plotting concentration of conjugate 1 versus percent growth of melanoma cells.
Figure 6:
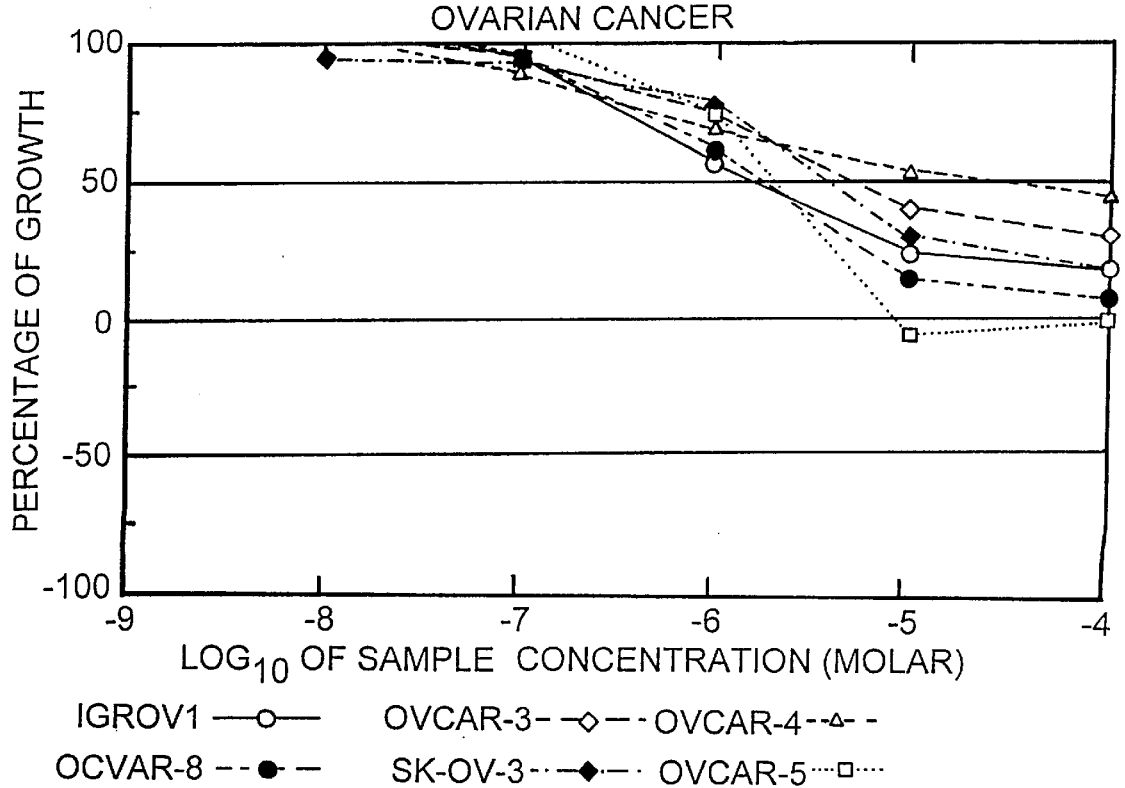
FIG. 6 is a graph plotting concentration of conjugate 1 versus percent growth of ovarian cancer cells.
Figure 7:
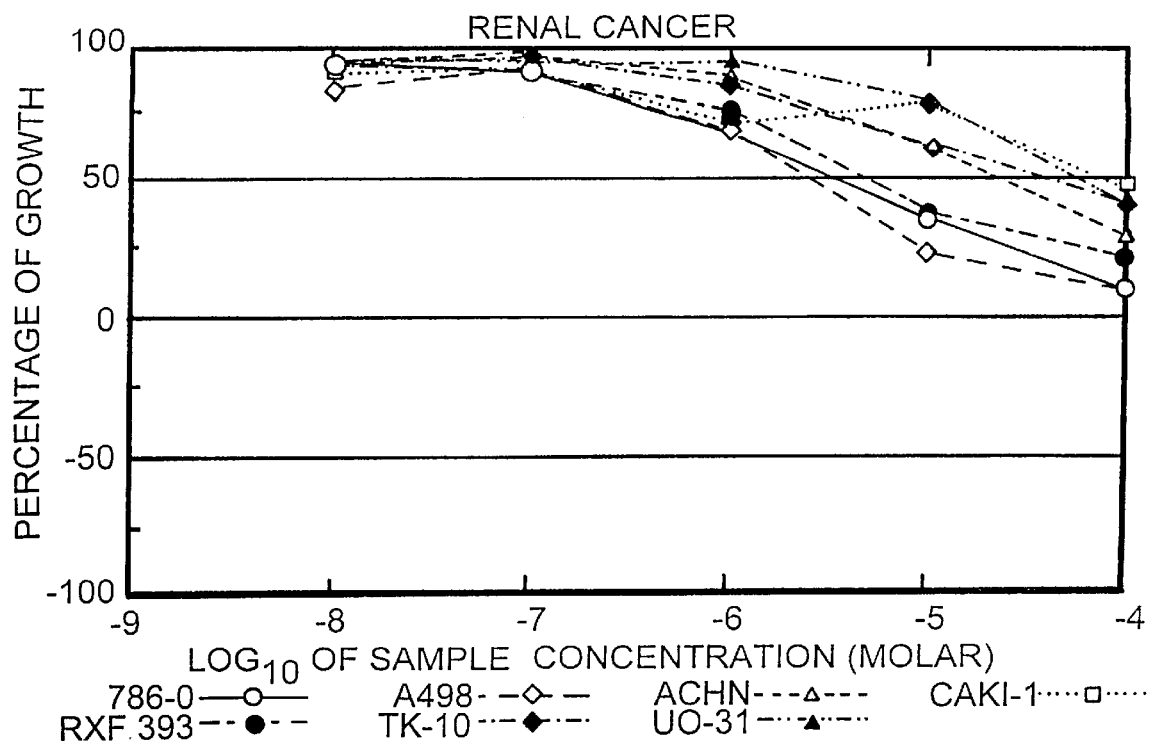
FIG. 7 is a graph plotting concentration of conjugate 1 versus percent growth of renal cancer cells.
Figure 8:
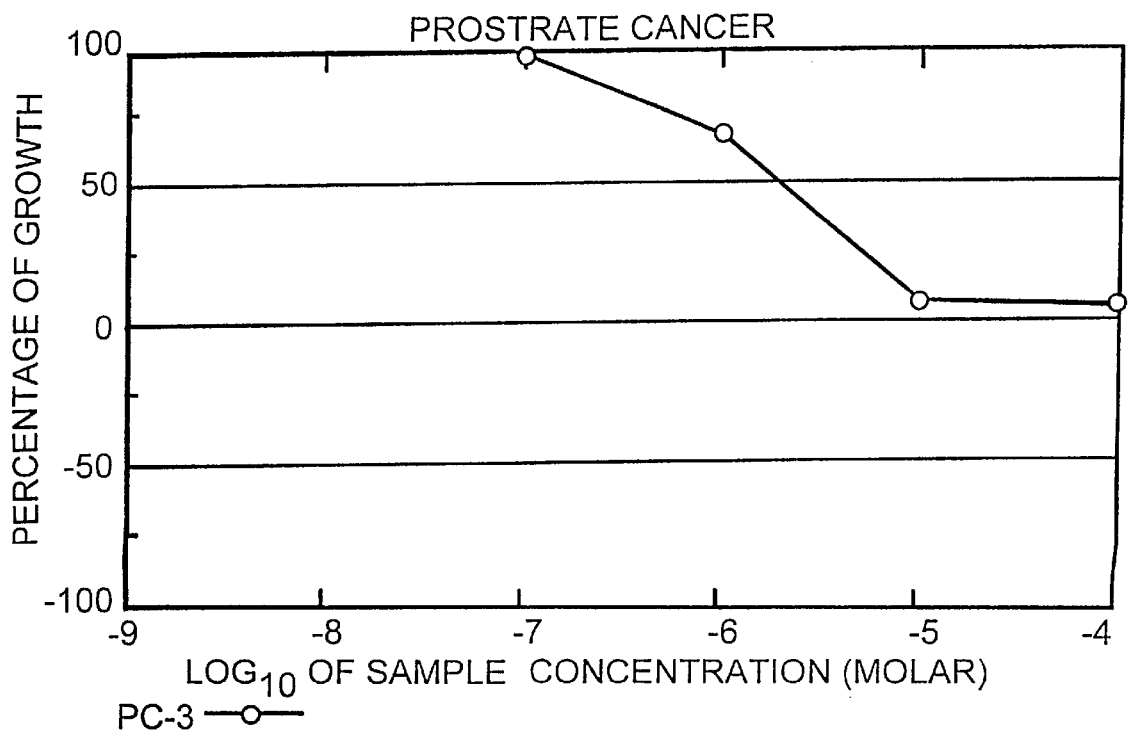
FIG. 8 is a graph plotting concentration of conjugate 1 versus percent growth of prostate cancer cells.
Figure 9:
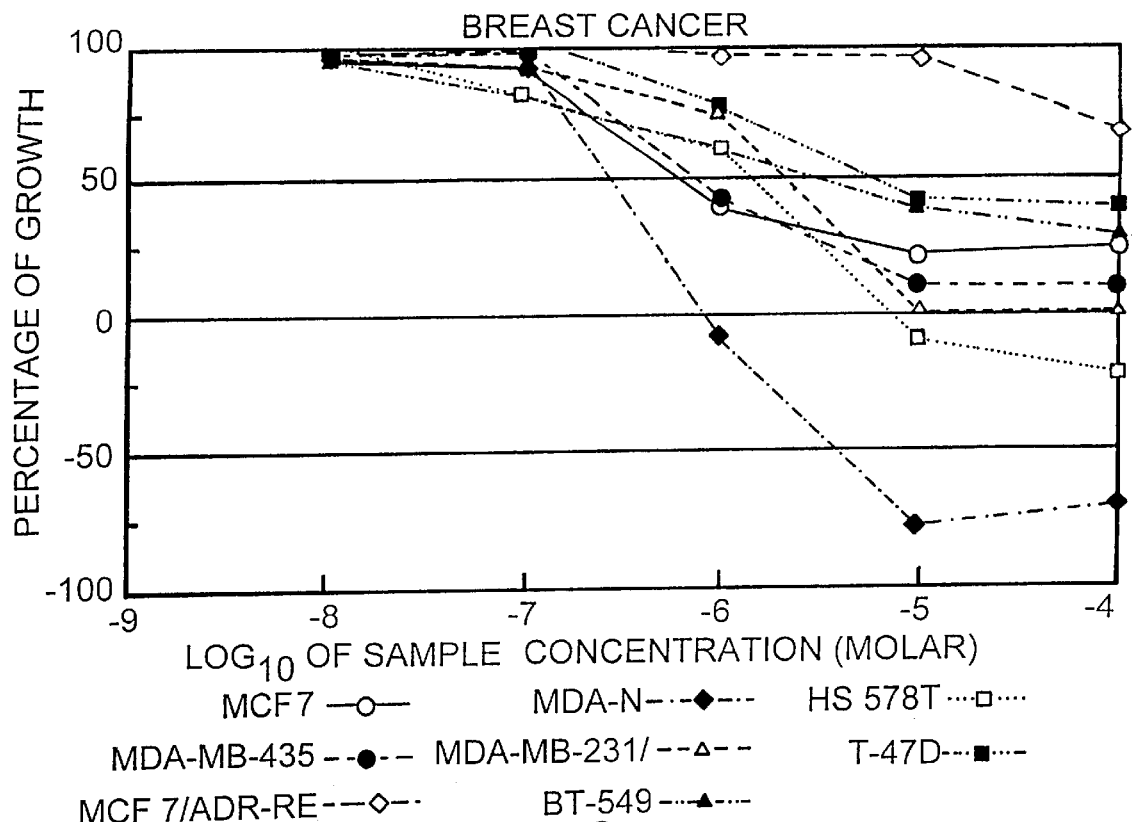
FIG. 9 is a graph plotting concentration of conjugate 1 versus percent growth of breast cancer cells.
Figure 10:
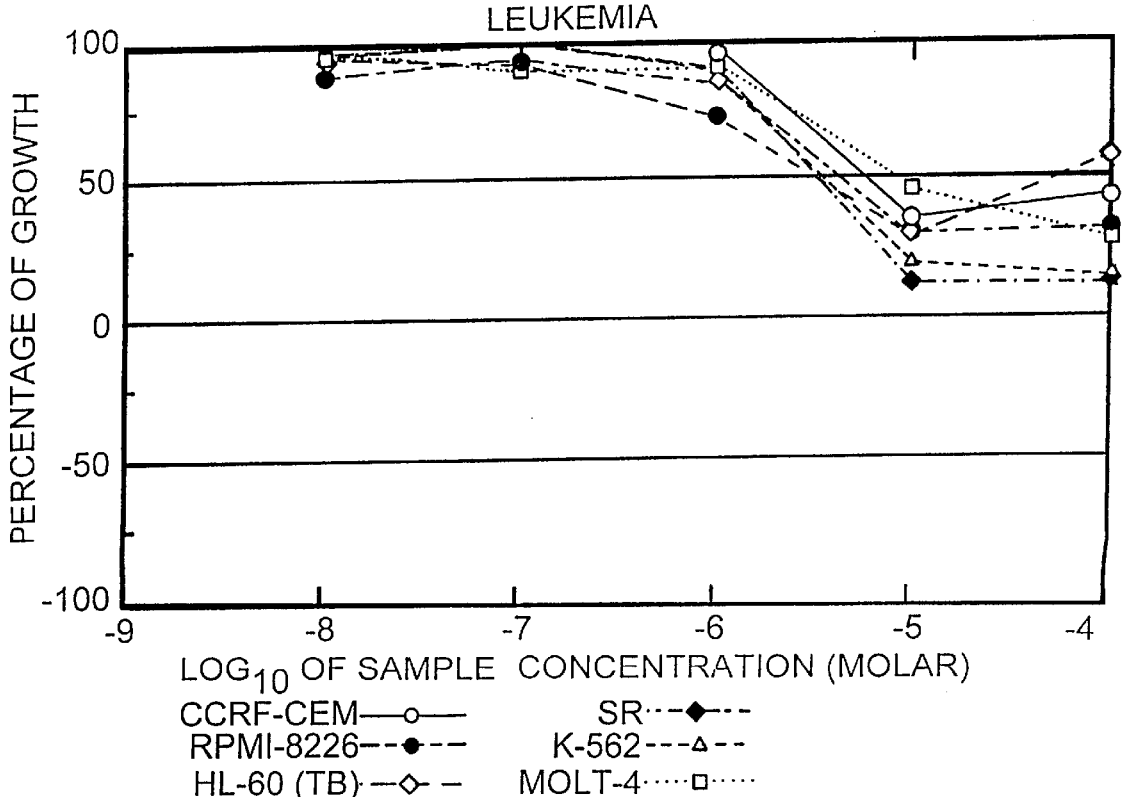
FIG. 10 is a graph plotting concentration of conjugate 2 versus percent growth of leukemia cells.
Figure 11:
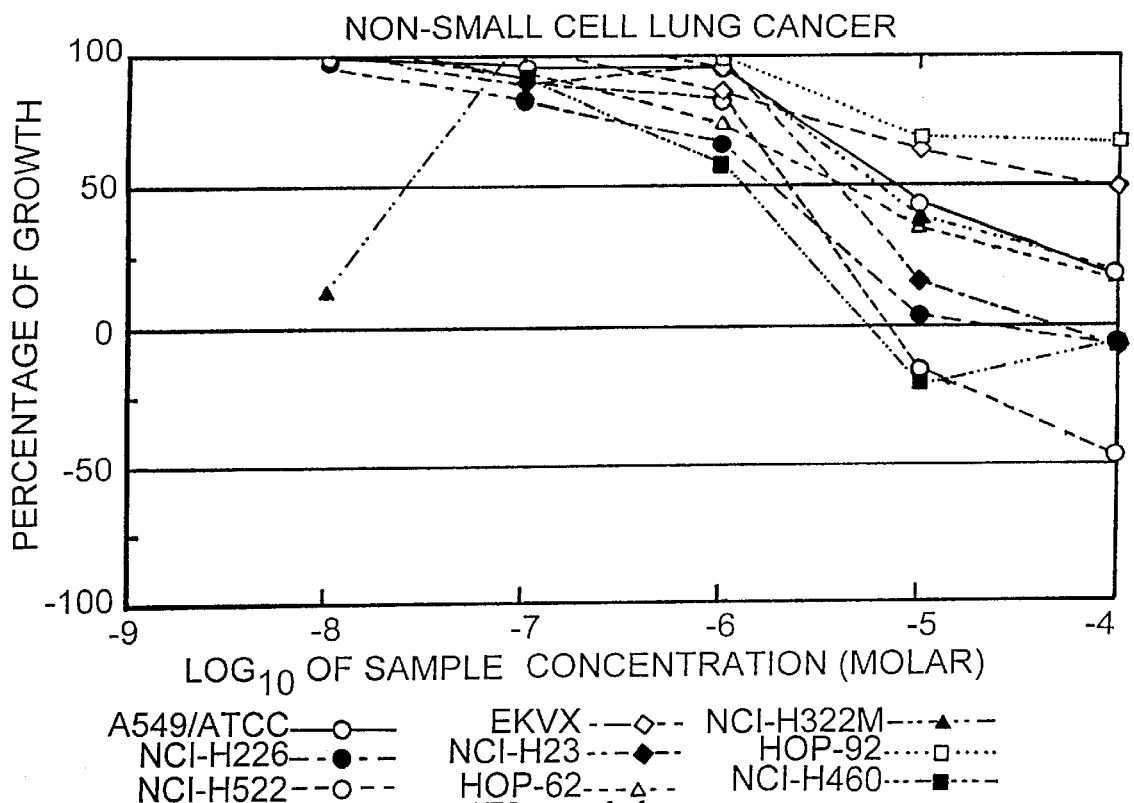
FIG. 11 is a graph plotting concentration of conjugate 2 versus percent growth of non-small cell lung cancer cells.
Figure 12:
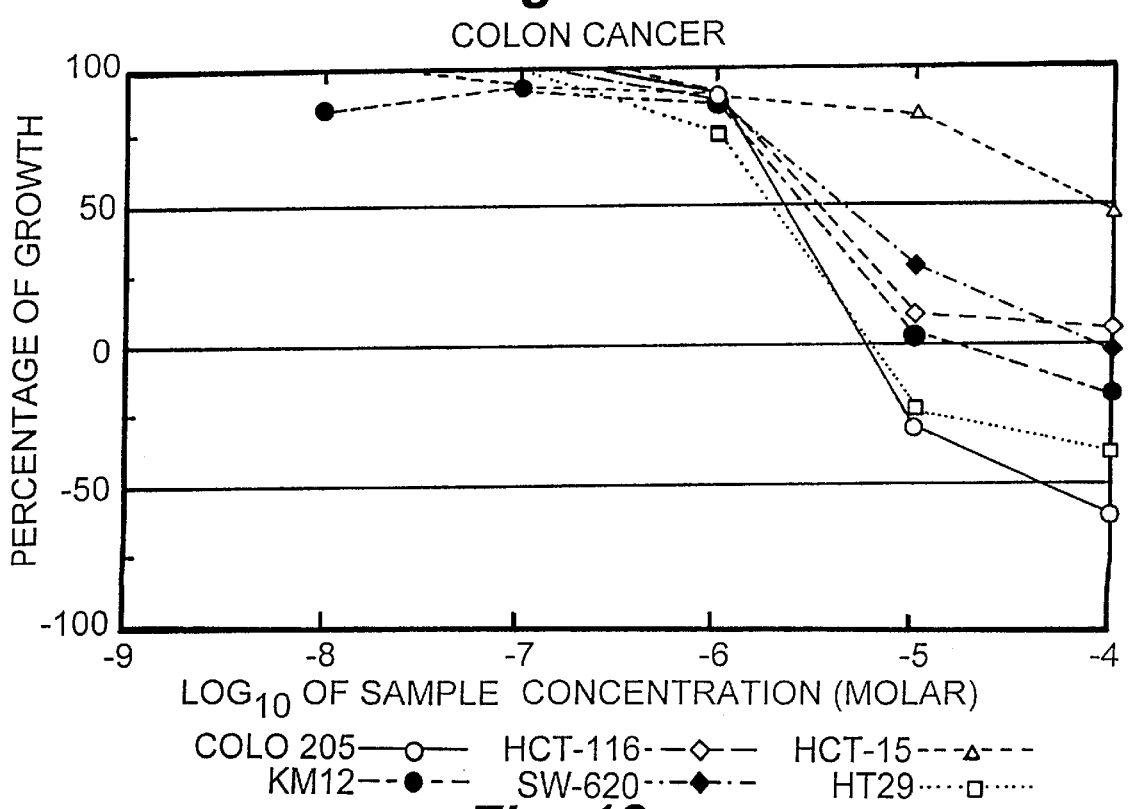
FIG. 12 is a graph plotting concentration of conjugate 2 versus percent growth of colon cancer cells.
Figure 13:
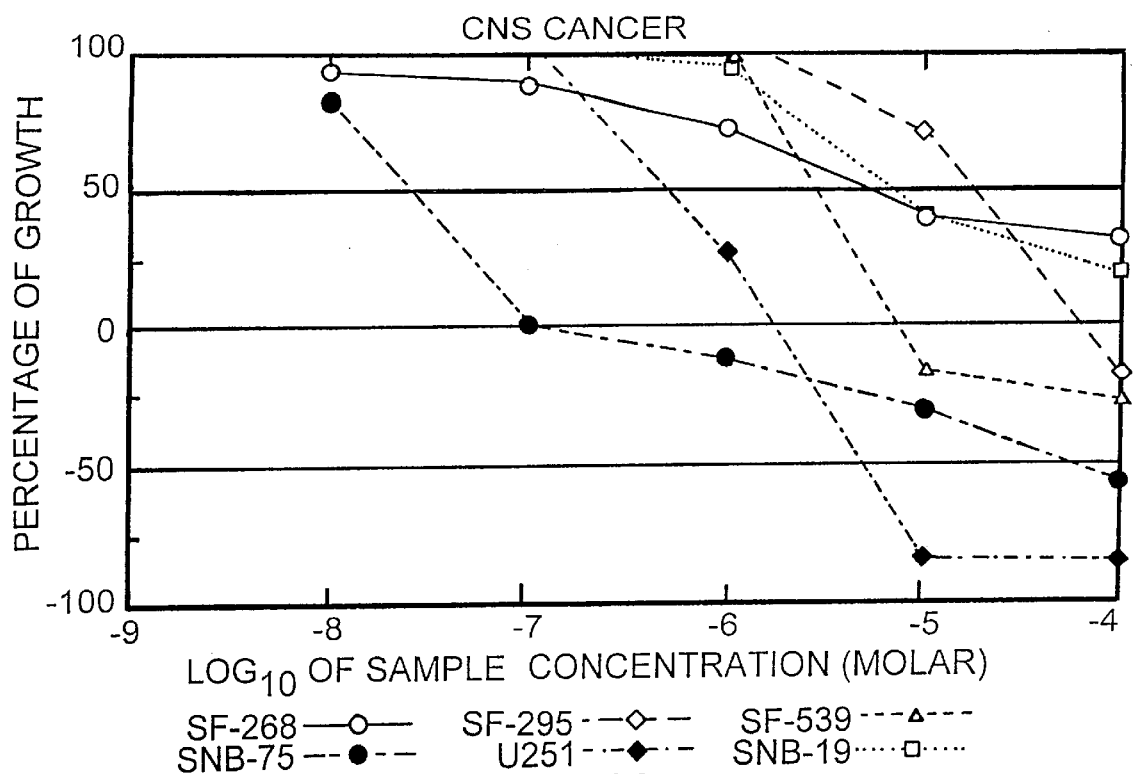
FIG. 13 is a graph plotting concentration of conjugate 2 versus percent growth of CNS cancer cells.
Figure 14:
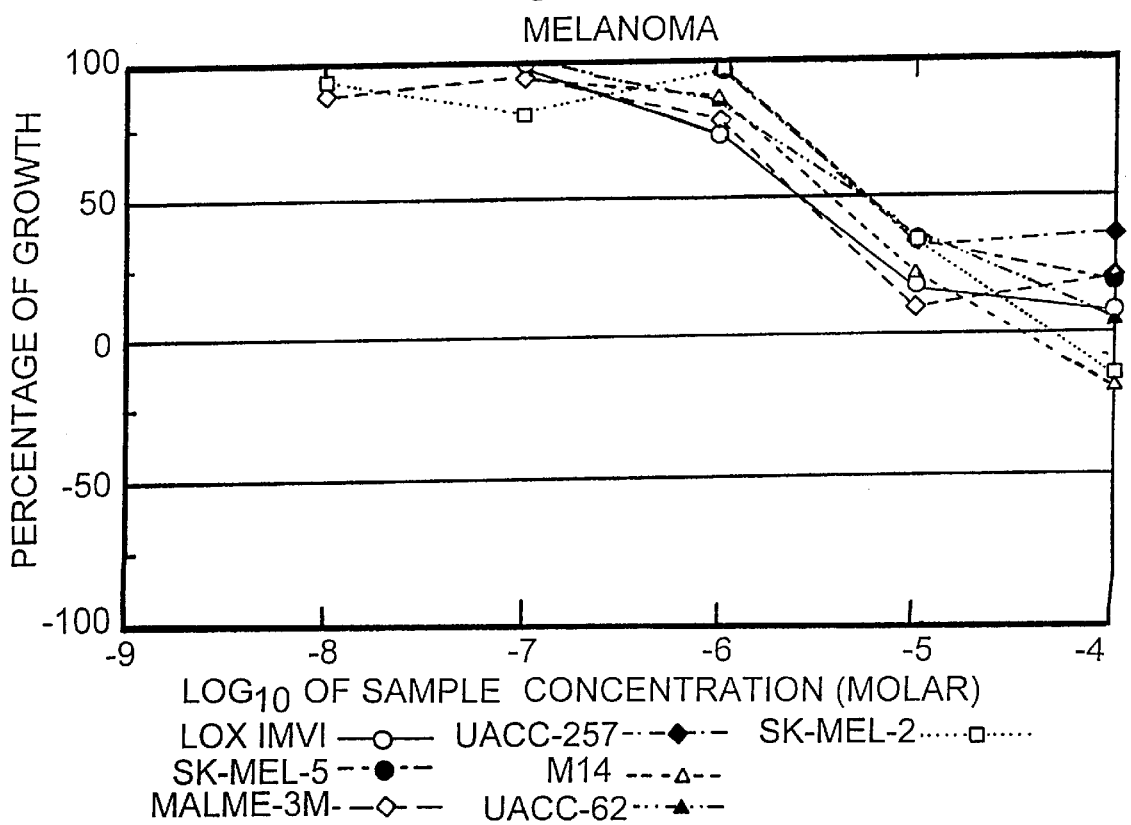
FIG. 14 is a graph plotting concentration of conjugate 2 versus percent growth of melanoma cells.
Figure 15:
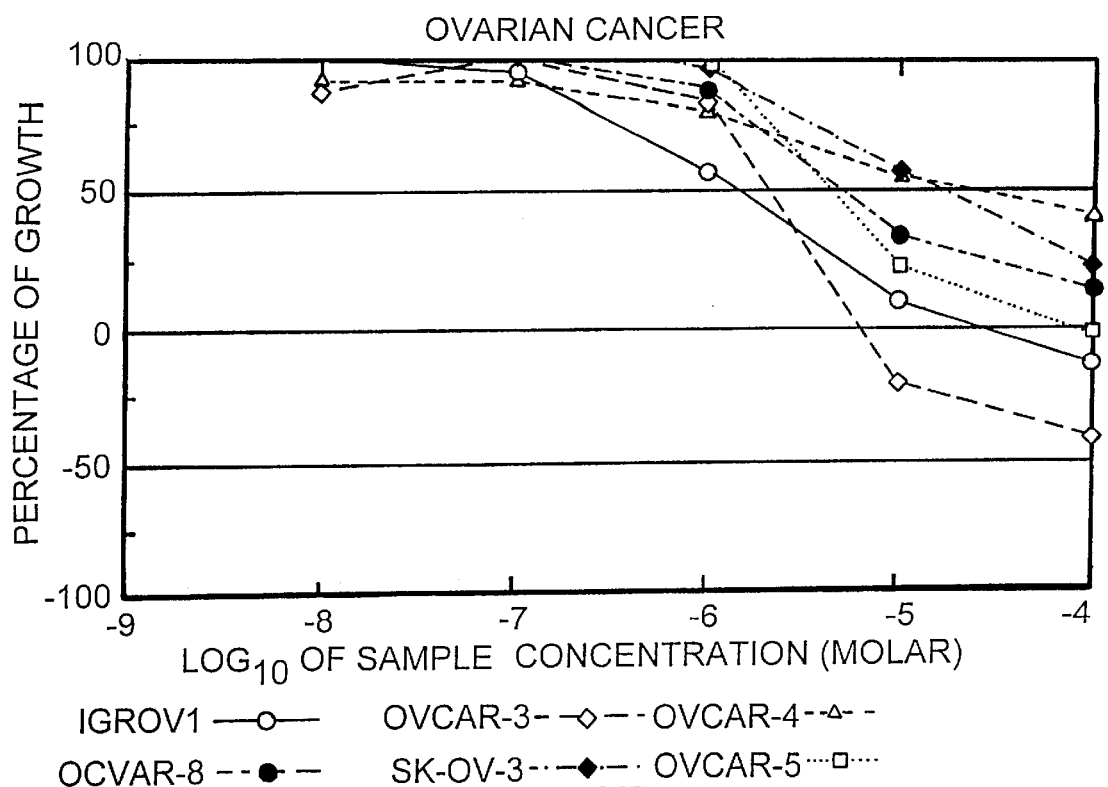
FIG. 15 is a graph plotting concentration of conjugate 2 versus percent growth of ovarian cancer cells.
Figure 16:
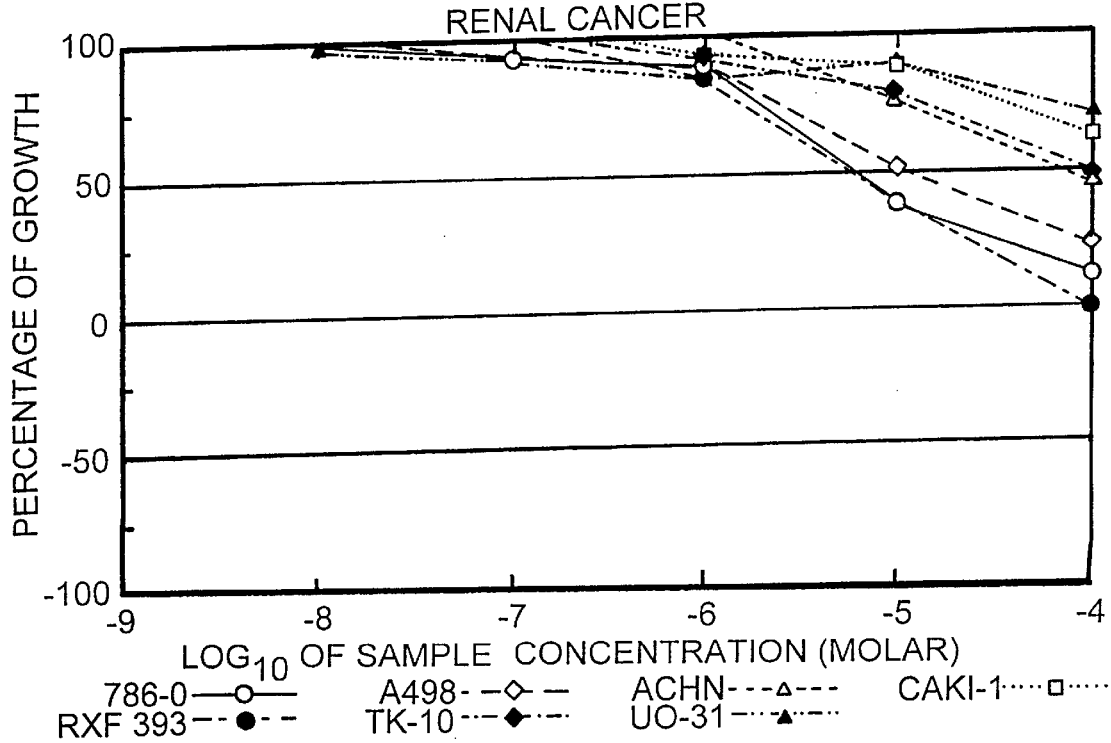
FIG. 16 is a graph plotting concentration of conjugate 2 versus percent growth of renal cancer cells.
Figure 17:
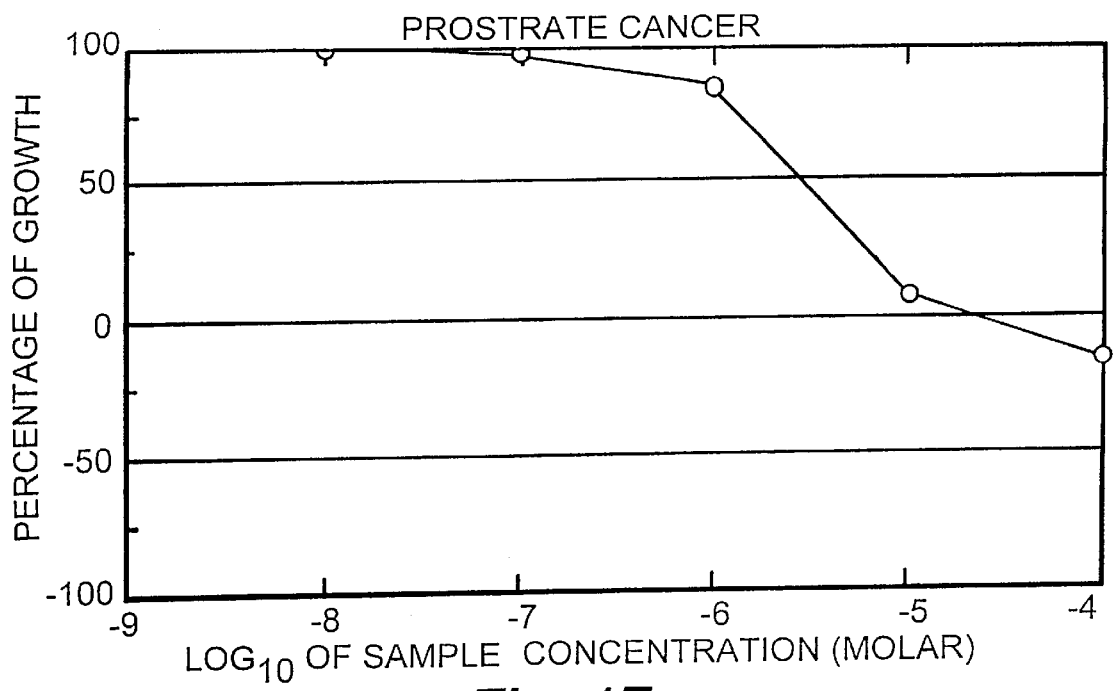
FIG. 17 is a graph plotting concentration of conjugate 2 versus percent growth of prostate cancer cells.
Figure 18:
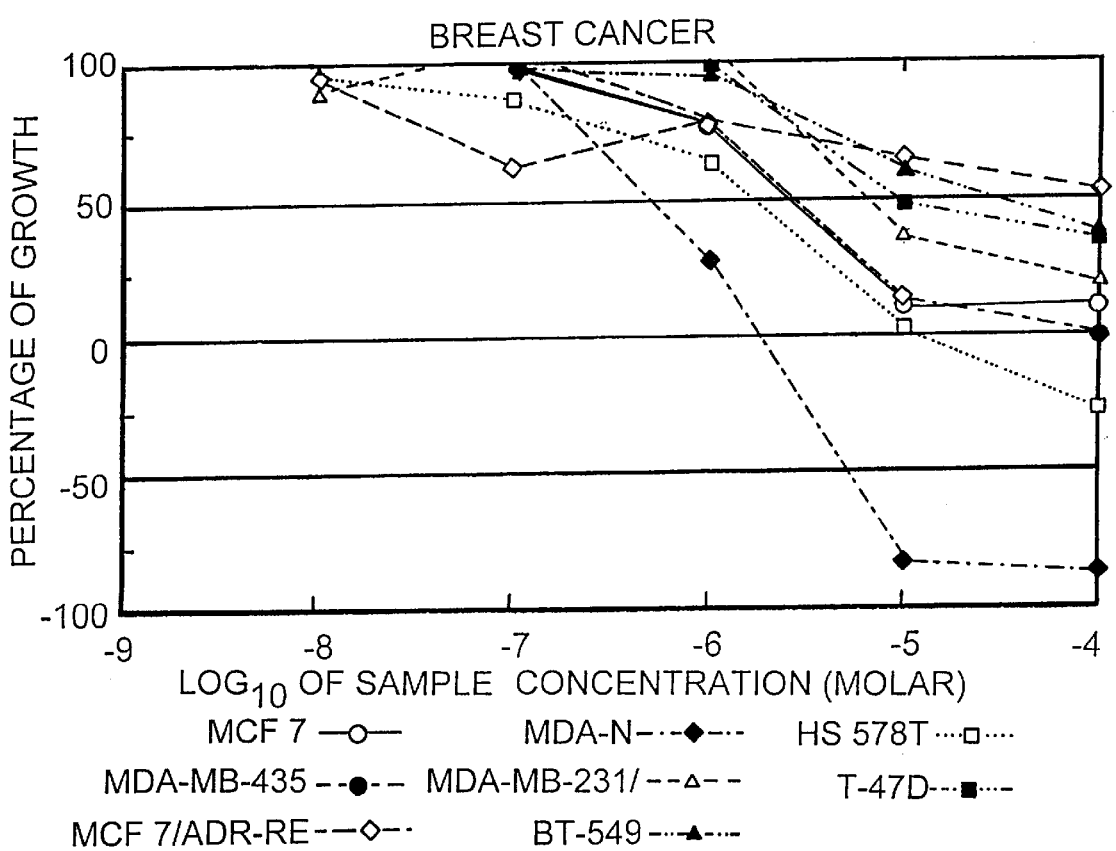
FIG. 18 is a graph plotting concentration of conjugate 2 versus percent growth of breast cancer cells.
Figure 19:
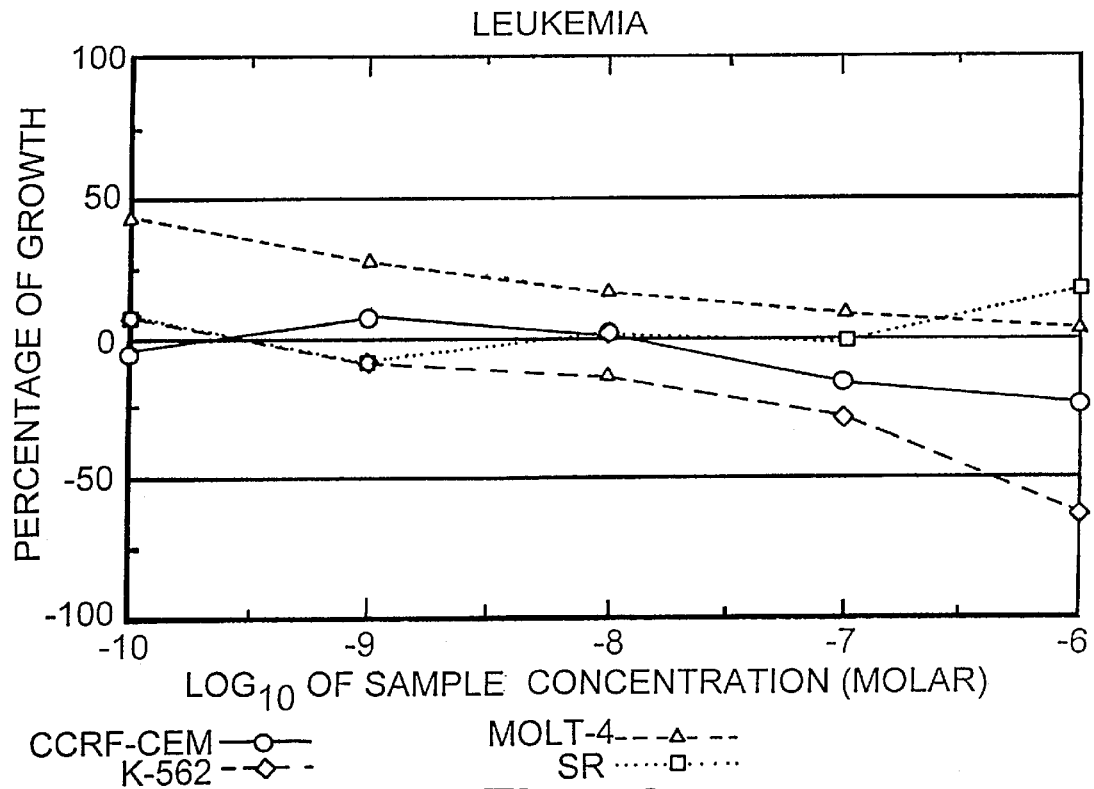
FIG. 19 is a graph plotting concentration of Taxol versus percent growth of leukemia cells.
Figure 20:
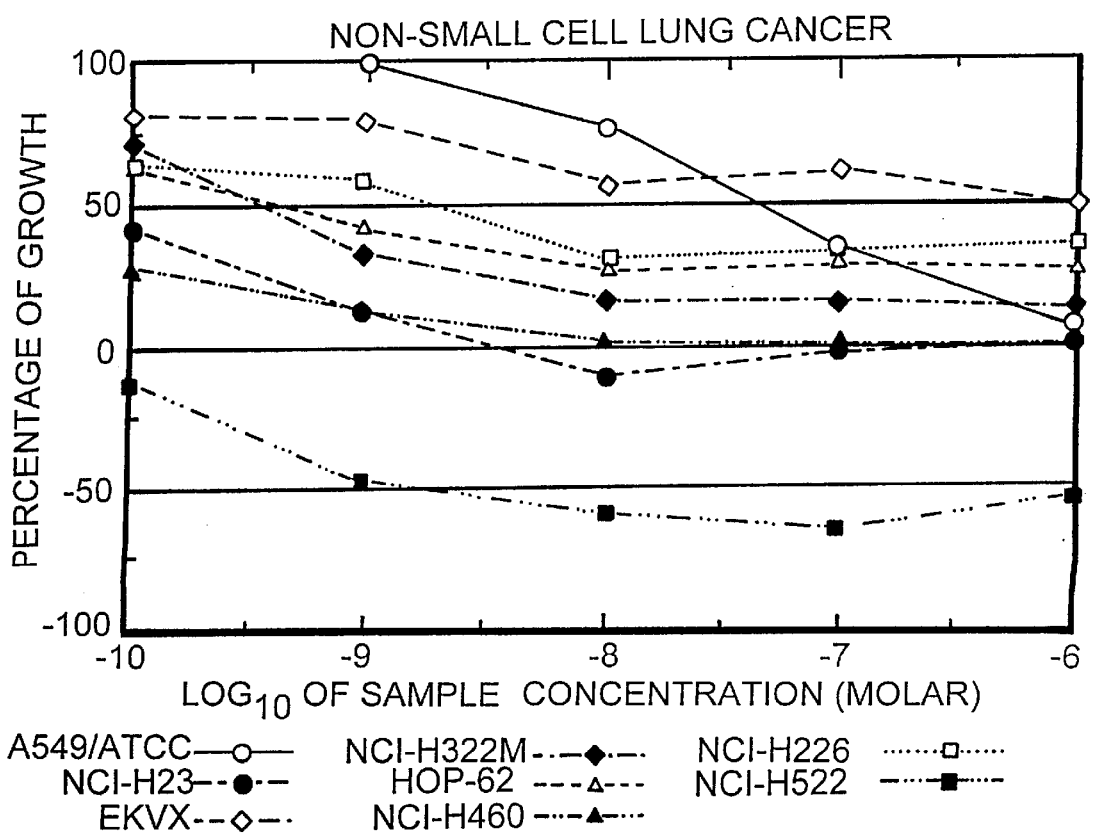
FIG. 20 is a graph plotting concentration of Taxol versus percent growth of non-small cell lung cancer cells.
Figure 21:
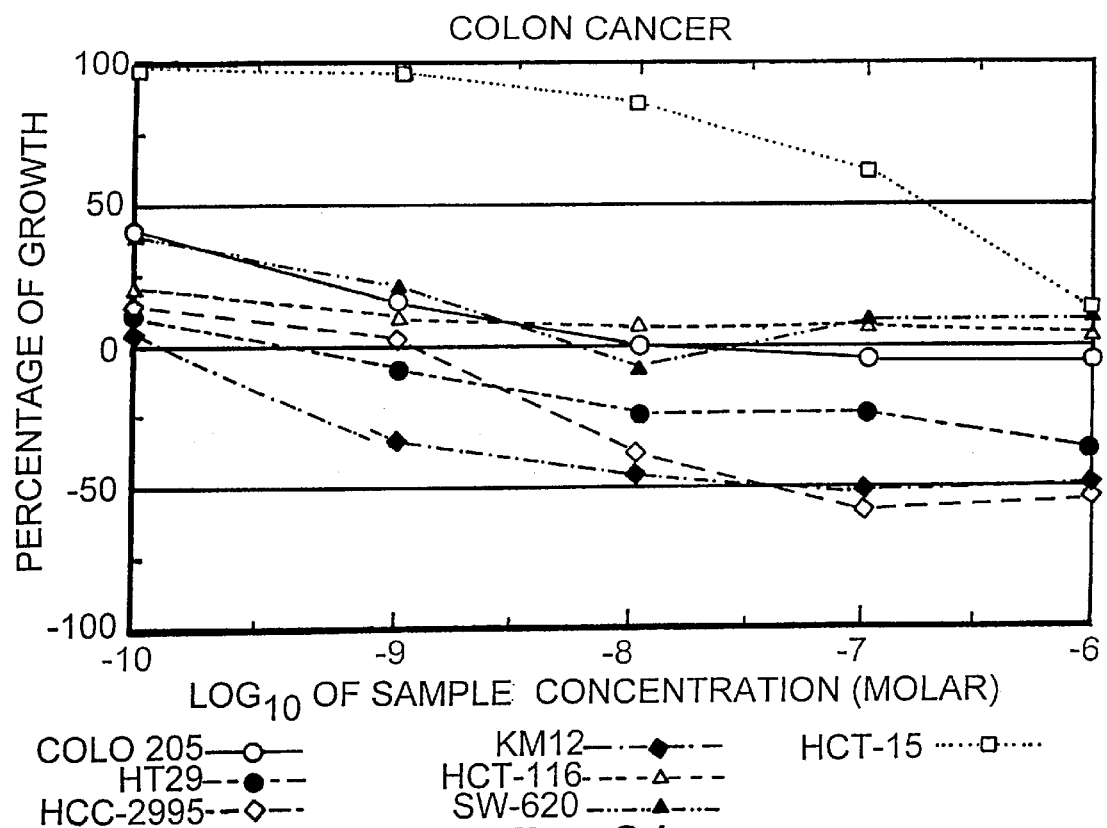
FIG. 21 is a graph plotting concentration of Taxol versus percent growth of colon cancer cells.
Figure 22:
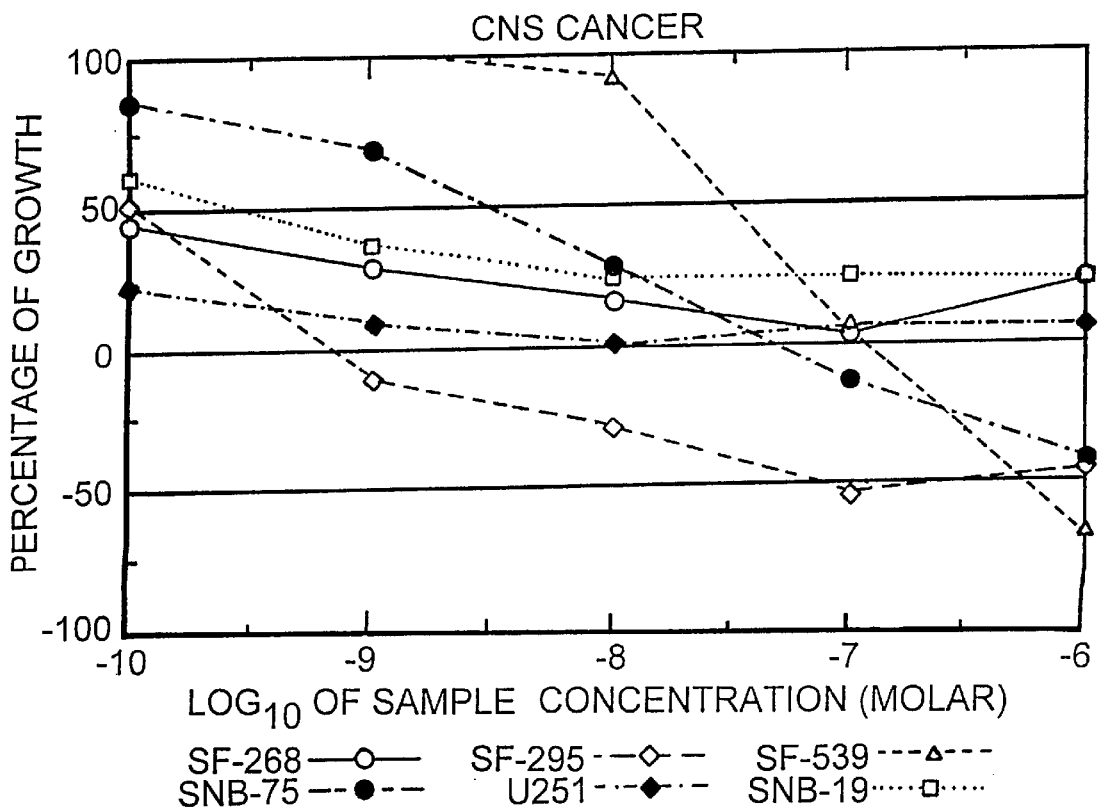
FIG. 22 is a graph plotting concentration of Taxol versus percent growth of CNS cancer cells.
Figure 23:
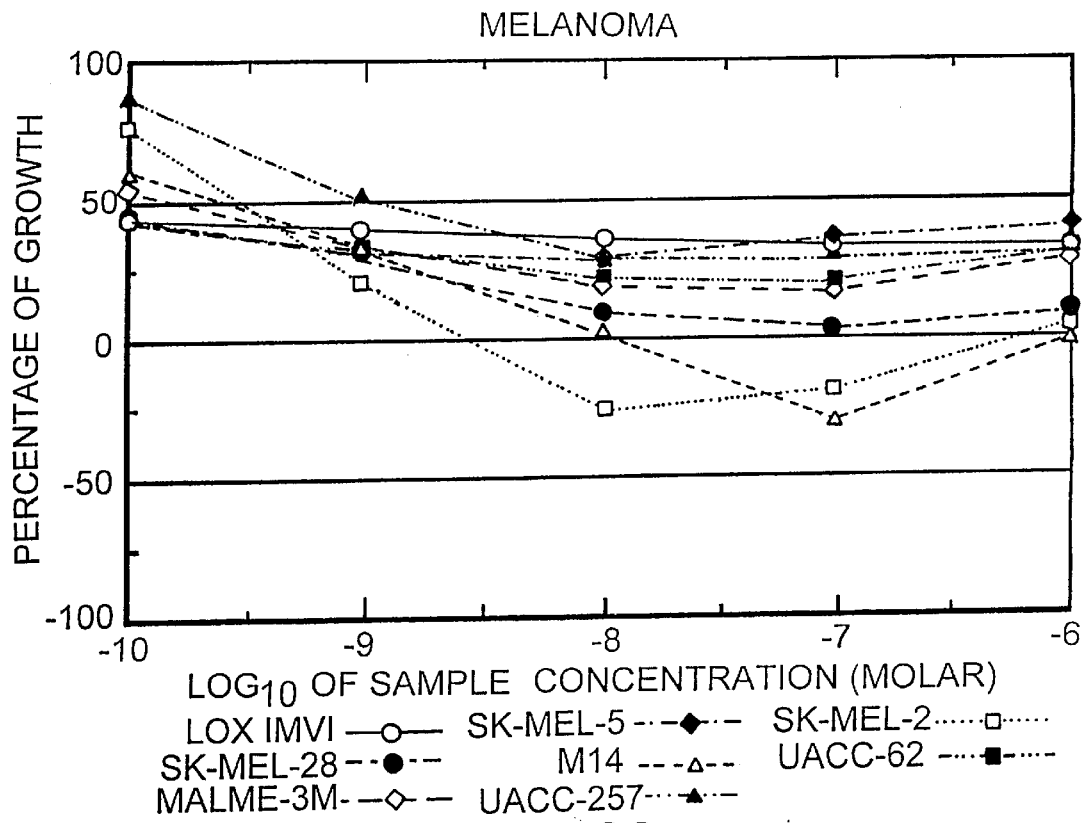
FIG. 23 is a graph plotting concentration of Taxol versus percent growth of melanoma cells.
Figure 24:
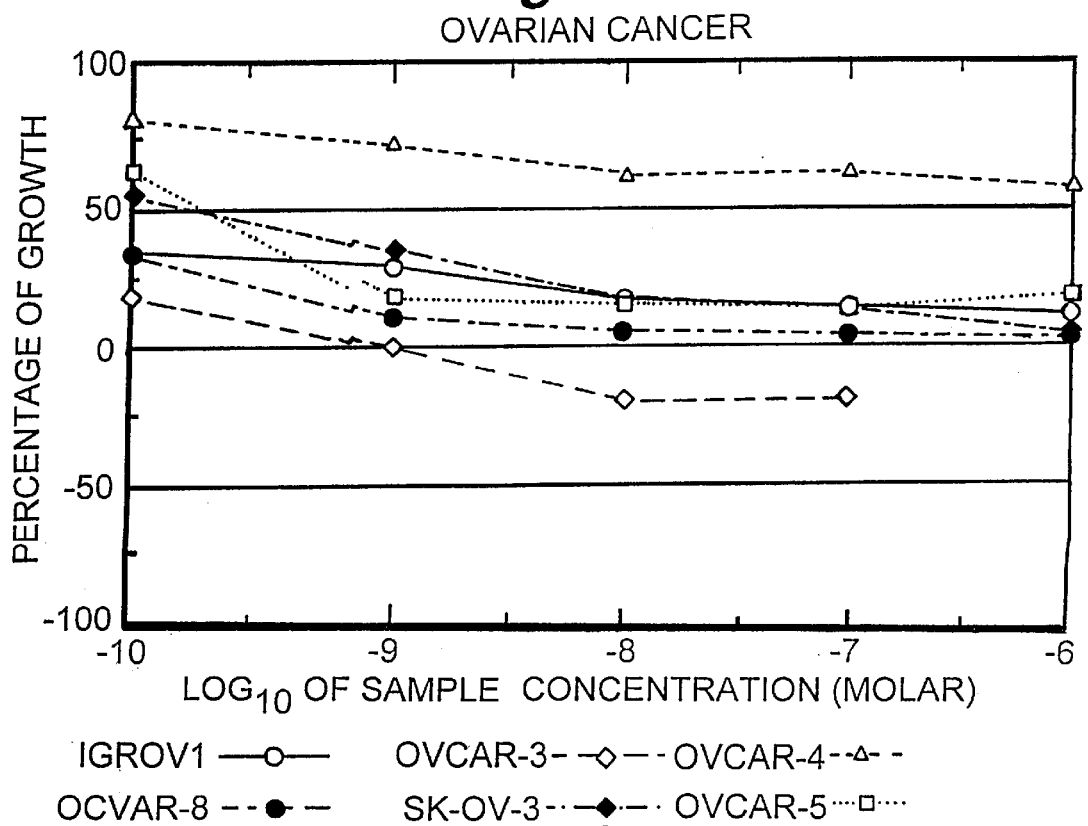
FIG. 24 is a graph plotting concentration of Taxol versus percent growth of ovarian cancer cells.
Figure 25:
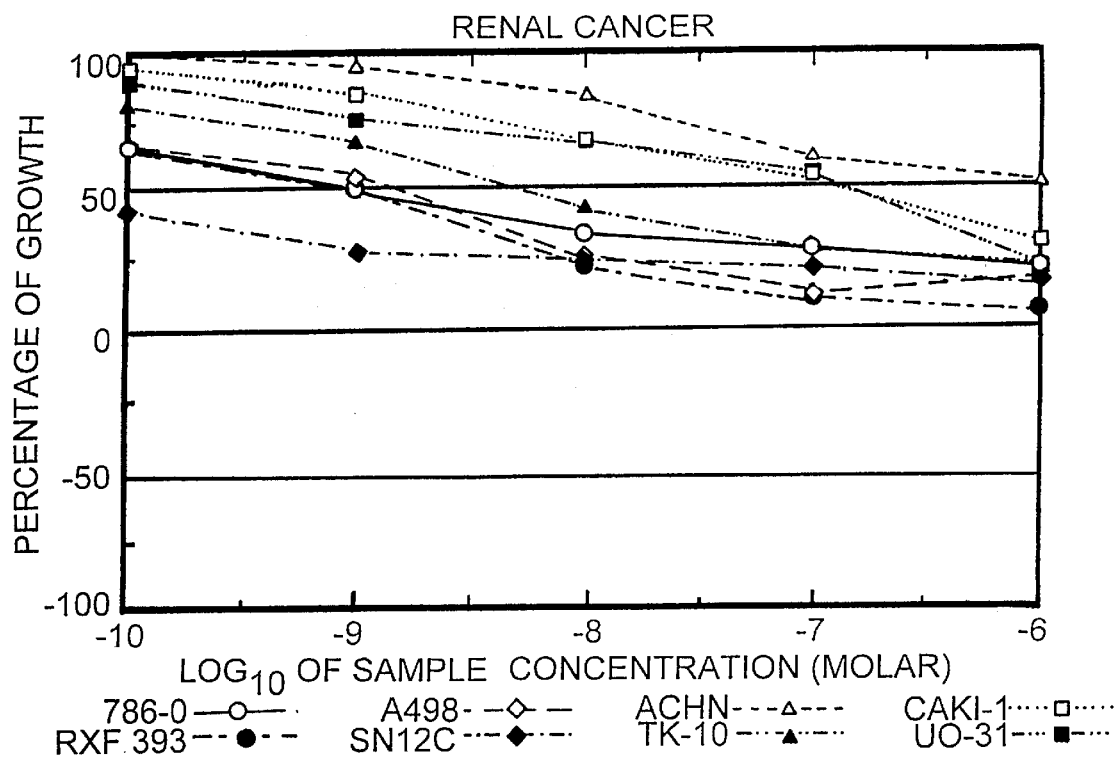
FIG. 25 is a graph plotting concentration of Taxol versus percent growth of renal cancer cells.
Figure 26:
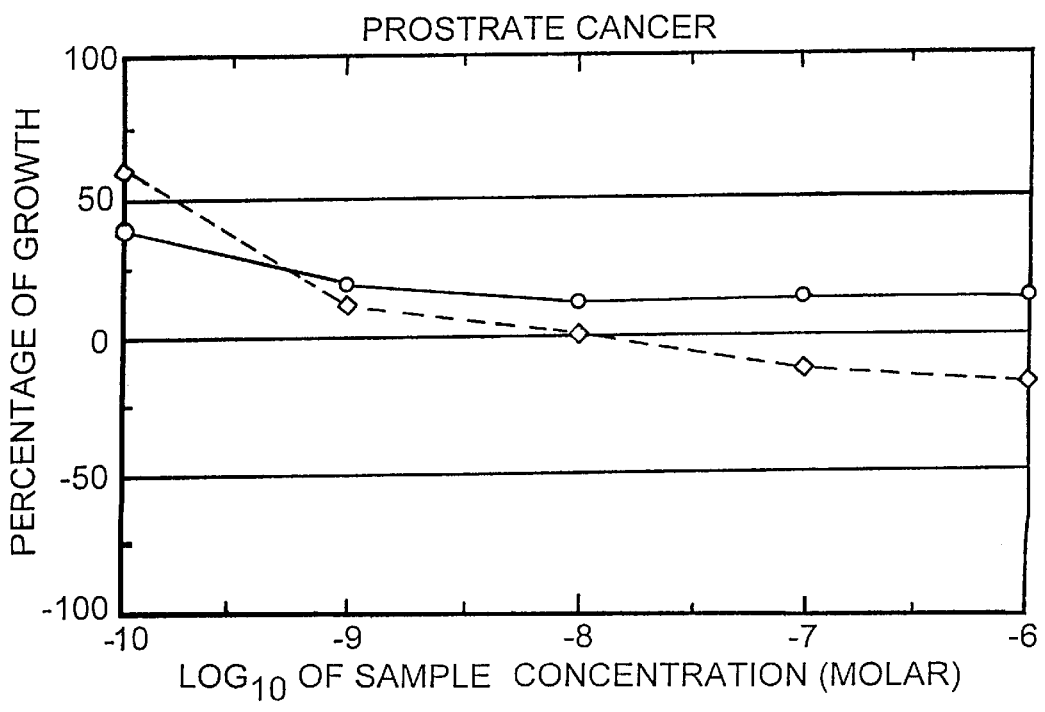
FIG. 26 is a graph plotting concentration of Taxol versus percent growth of prostate cancer cells.
Figure 27:
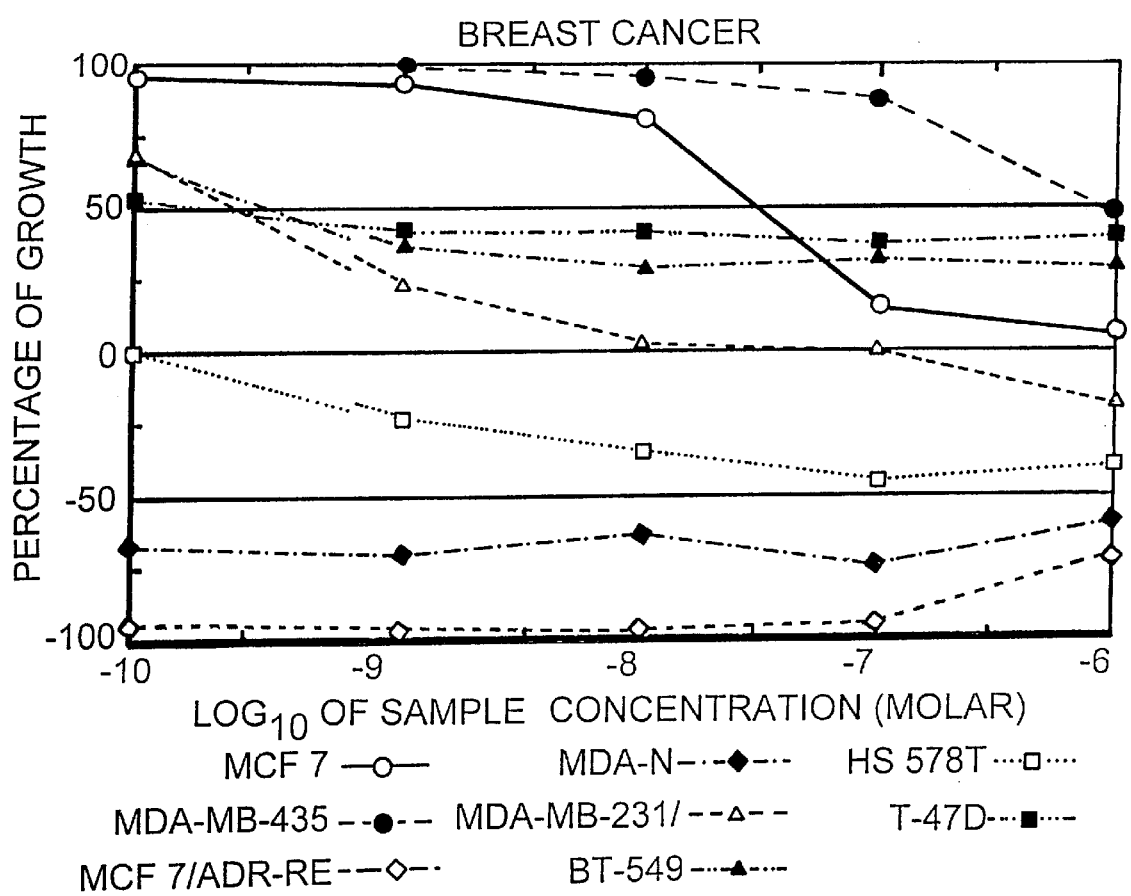
FIG. 27 is a graph plotting concentration of Taxol versus percent growth of breast cancer cells.

The activities of conjugates 1 and 2 were tested against 57 cancer cell lines. The results are presented in FIGS. 1–9 for conjugate 1, FIGS. 10–18 for conjugate 2 and FIGS. 19–27 for Taxol.

To understand the data, reference is made to the guides provided by the NCI, excerpted as follows:

The Calculated Measurement of Effect: Percentage Growth (PG)

The measured effect of the compound on a cell line is currently calculated according to one or the other of the following two expressions:

If (Mean $OD_{test}$–Mean $OD_{tzero}$)≥0, then $PG=100\times$(Mean $OD_{test}$–Mean $OD_{tzero}$)/(Mean $OD_{ctrl}$–Mean $Od_{tzero}$)

If (Mean $OD_{test}$–Mean $OD_{tzero}$)<0, then $PG=100 \times$(Mean $OD_{test}$–Mean $Od_{tzero}$)/Mean $Od_{tzero}$ Where:

Mean $OD_{tzero}$=The average of optical density measurements of SRB-derived color just before exposure of cells to the test compound.

Mean $OD_{test}$=The average of optical density measurements of SRB-derived color after 48 hours exposure of cells to the test compound.

Mean $OD_{ctrl}$=The average of optical density measurements of SRB-derived color after 48 hours with no exposure of cells to the test compound.

Experimental data was collected against each cell line. Each concentration is expressed as the $\log_{10}$ (molar or μg/ml). The response parameters GI50, TGI, and LC50 are interpolated values representing the concentrations at which the PG is +50, 0, and −50, respectively. Sometimes these response parameters cannot be obtained by interpolation. If, for instance, all of the PGs in a given row exceed +50, then none of the three parameters can be obtained by interpolation. In such a case, the value given for each response parameter is the highest concentration tested. This practice is extended similarly to the other possible situations where a response parameter cannot be obtained by interpolation.

Dose-Response Curves

The dose-response curve page of the data package is created by plotting the PGs against the $\log_{10}$ of the corresponding concentration for every cell line. The cell line curves are grouped by subpanel. Horizontal lines are provided at the PG values of +50, 0, and −50. The concentrations corresponding to points where the curves cross these lines are the GI50, TGI and LC50, respectively.

Several important distinctions are apparent from the data. Most important, the patterns of anticancer actively for conjugates 1 and 2 differ from that of Taxol. In one sense, conjugates 1 and 2 are effective anticancer agents against a more restricted set of cancer cell lines. For example, conjugates 1 and 2 were not very effective against any of the six leukemia cancer cell lines tested, whereas Taxol was somewhat effective against all four leukemia cell lines against which Taxol was tested. (See FIGS. 1, 10 and 19.)

The relative activity against members within a class of cancers also was altered. For example, at TGI (horizontal line at zero in the graphs), Taxol was more effective against non-small cell lung cancer line H522 than against H460 (by about 3 logs), whereas conjugates 1 and 2 were slightly more effective against H460 than H522. As another example, Taxol was least effective at TGI against CNSU251, whereas conjugate I was most effective against CNSU251 and conjugate 2 was also very effective against CNSU251 (relative to other CNS cell lines). As a further example, Taxol was equivalent in activity toward MDA-N and MDA-MB-435 breast cancer cell lines at all concentrations tested, whereas conjugates 1 and 2 were more effective against MDA-N than MDA-MB-435 at all concentrations tested.

To further illustrate the differences in the activity of conjugates 1 and 2 versus that of Taxol, the NCI subjected the data to a statistical analysis designed by the NCI to reflect differences in the pattern of activity of anticancer agents. Conjugate 1 and conjugate 2 were determined to be statistically different in their pattern of activity versus Taxol in this unique measurement by the NCI.

It also is to be noted that, in general, conjugates 1 and 2 were one thousand to ten thousand times less potent than Taxol for many cell lines tested. This reduction in activity is important, especially since conjugates 1 and 2 maintained strong activity against some cell lines. Conjugates 1 and 2 will be sufficiently active against certain cell lines, but will have, on average, a substantially and disproportionately lower activity against other cell lines, reducing the potential for side effects. For example, the TGI for Taxol against CNS SF-539 is −6.95, and the TGI for conjugate 1 against this cell line is −5.13 and for conjugate 2 is −5.53. (In other words, the activity of the conjugates was reduced versus that of Taxol by less than 2 logs). The GI50 for Taxol against CNS SF 539 is −7.52, whereas the GI50s for conjugates 1 and 2 are −6.22 and −5.56, respectively (again less than 2 logs difference). In contrast, Taxol has a GI50 for cell line CNSSF 268 of less than −10.0, whereas analogs 1 and 2 have GI50s for CNSSF 268 of 5.36 and 5.28, respectively. This represents a reduction of activity in the conjugates vs. that of Taxol by at least about 5 logs activity! On average, the GI50 for Taxol across all cell lines tested is at least −9.19. (It is probably much higher since concentrations less than −10 were not tested, and if Taxol was active at −10.0, −10 (instead of the actual lower value) was used in calculating the average of −9.19. There were 27 instances when this occurred.) The average GI50s for conjugates 1 and 2, on the other hand, were 5.49 and 5.22, respectively. Therefore, the average difference in activity for Taxol vs. the conjugates is at least between 3 and 4 logs. Thus, the sharp reduction in the activity of the conjugates against many cell lines vs. a lesser reduction for other cell lines is expected to reduce the potential side effects of the conjugates versus those of Taxol at effective doses.

Cancers other than CNS, breast and colon cancer can be treated. For example, there was activity against non-small cell lung cancer cells, melanoma cells and ovarian cancer cells. However, the activity was relatively reduced and was extremely specific, limiting the utility of the conjugates for treating generally such cancers. In any event, cancer patients could be evaluated to determine if conjugates 1 and 2 are strongly active against the patient's cancer prior to selecting conjugates 1 or 2 as the anti-cancer agent of choice for that patient.

The foregoing experiments establish that the conjugates of the invention have altered specificity versus that of Taxol for cancer cell lines. Because of this altered specificity, it also is clear that the conjugates themselves are gaining access into the target cells (as opposed to simply releasing Taxol into the environment outside of the cell). Thus, the DHA moiety appears to selectively target certain cell types as opposed to others. The ability of the conjugates to gain entry into the targeted cells was unknown prior to the invention, and the ability of the DHA moiety to selectively target certain cell types was unexpected.

The compounds useful in the invention may be delivered in the form of anti-cancer cocktails. An anti-cancer cocktail is a mixture of any one of the compounds useful with this invention with another anti-cancer agent such as an anti-cancer drug, a cytokine, and/or supplementary potentiating agent(s). The use of cocktails in the treatment of cancer is routine. In this embodiment, a common administration vehicle (e.g., pill, tablet, implant, injectable solution, etc.) would contain both the conjugate useful in this invention and the anti-cancer drug and/or supplementary potentiating agent.

Anti-cancer agents include anti-cancer drugs. Anti-cancer drugs are well known and include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1 ; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-cancer drugs include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone +pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Supplementary potentiating agents likewise are well characterized and include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as verapamil, cyclosporin A and Cremaphor EL.

The compounds of the invention also can be administered with cytokines such as granulocyte colony stimulating factor.

The compounds of the invention, when used in cocktails, are administered in therapeutically effective amounts. A therapeutically effective amount will be determined by the parameters discussed below; but, in any event, is that amount which establishes a level of the drug(s) in the area of the tumor which is effective in inhibiting the tumor growth.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

The active compounds of the present invention may be a pharmaceutical composition having a therapeutically effective amount of a conjugate of the invention optionally included in a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy.

Compositions suitable for parenteral administration conveniently comprise a sterile preparation of the conjugates of the invention. This preparation may be formulated according to known methods. Formulations for Taxol and other taxanes can be found in Chapter 9 of *Taxol: Science and Applications,* CRC Press, Inc., 2000 Corporate Boulevard, N.W., Boca Raton, Fla. 33431. In general, Taxol has been formulated as a 6 mg/ml cremophor EL (polyoxyethylated castor oil)/ethanol mixture, which is diluted to final volume with normal saline or 5% dextrose. A 15 mg/ml solution of taxotere has been formulated in polysorbate 80 (polyoxyethylene sorbitanmonooleate)/ethanol mixture, diluted with 5% dextrose.

The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in *Remington's Pharmaceutical Sciences,* Mack Publishing Company, Easton, Pa.

The invention is used in connection with treating subjects having, suspected of having, developing or suspected of developing cancer. A subject as used herein means humans, primates, horses, cows, pigs, sheep, goats, dogs, cats and rodents.

The conjugates of the invention are administered in effective amounts. An effective amount means that amount necessary to delay the onset of, inhibit the progression of or halt altogether the onset or progression of the particular condition being treated. In general, an effective amount will be that amount necessary to inhibit mammalian cancer cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosage may be adjusted appropriately to achieve desired drug levels, locally or systemically. Generally, daily oral doses of active compounds will be from about 0.01 mg/kg per day to 1000 mg/kg per day. It is expected that IV doses in the range of about 1 to 1000 mg/m$^2$ per day will be effective. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day are contemplated to achieve appropriate systemic levels of compounds.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion. Intravenous routes are preferred.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating solid tumors by placing the implant near or directly within the tumor, thereby affecting localized, high-doses of the compounds of the invention.

We claim as follows:

1. A composition of matter comprising
   a covalent conjugate of cis-docosahexaenoic acid and paclitaxel.

2. The composition of matter of claim 1, wherein the composition is

4. A pharmaceutical composition comprising
   a conjugate of cis-docosahexaenoic acid and paclitaxel, and
   a sterile, pharmaceutically acceptable carrier.

5. The pharmaceutical composition of claim 4, wherein the conjugate is

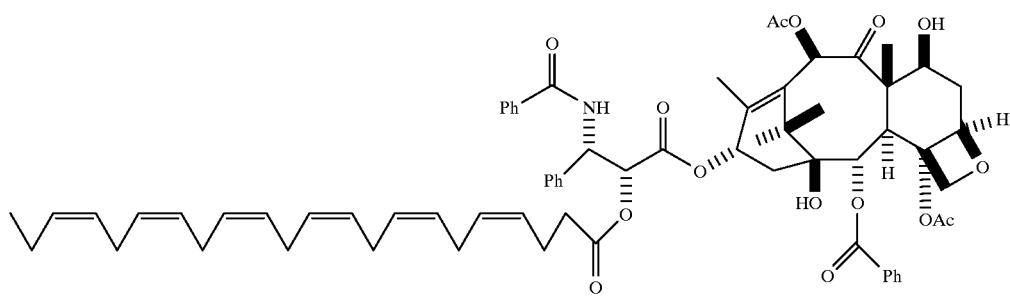

3. The composition of matter of claim 1, wherein the composition is

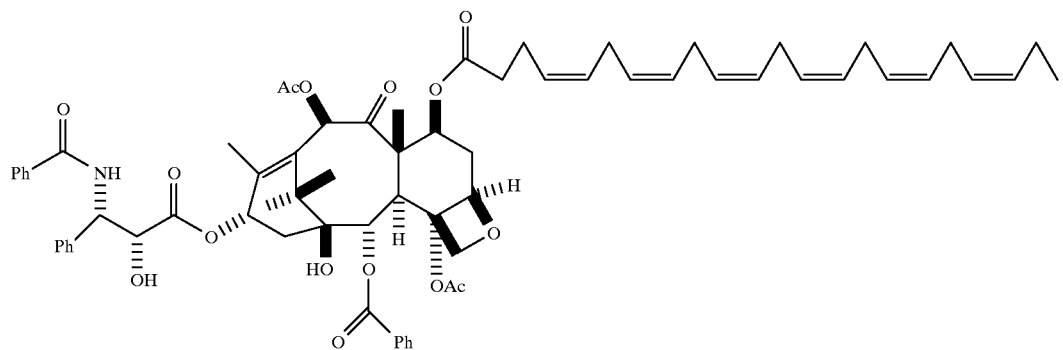

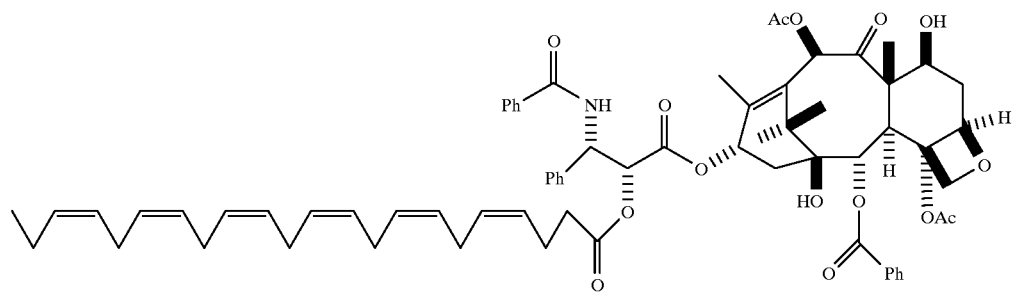

6. The pharmaceutical composition of claim 4, wherein the conjugate is

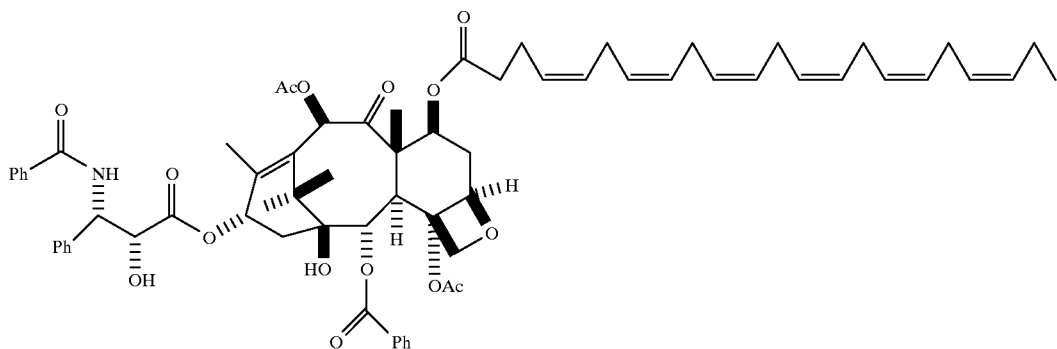

7. The pharmaceutical composition of claim 4 further comprising an anti-cancer agent other than the conjugate.

8. The pharmaceutical of claim 7 wherein the anti-cancer agent is selected from the group consisting of:

Aminoglutethimide; Asparaginase; Bleomycin; L-Buthiamine Sulfoxide; Busulfan; Camptothecin; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Edatrexate; Estramustine phosphate sodium; Etoposide (V16-213); Floxuridine; Fluorouracil (5-FU); Flutamide; Gallium Nitrite; Hydroxyurea (hydroxycarbamide); Idarubicin; Ifosfamide; Interferon Alfa-2a, Alfa 2b; Leuprolide acetate (LHRH-releasing factor analogue); Lomustine (CCNU); Mechlorethamine HCl (nitrogen mustard); Megestrol; melphalan; Mercaptopurine; Methotrexate (MTX); Mitomycin; Mitotane (o.p'-DDD); Mitoxantrone HCl; Octreotide; Plicamycin; Prednisone; Procarbazine HCl; Streptozocin; Tamoxifen citrate; Taxanes; Taxiods; Thioguanine; Thiotepa; Tiasofuran; Topotecan; Vinblastine sulfate; Vincristine sulfate; Amsacrine (m-AMSA); Azacitidine; Hexamethylmelamine (HMM); Interleukin 2; Mitoguazone (methyl-GAG); Methyl glyoxal bis-guanylhydrazone (MGBG); Pentostatin; Semustine (methyl-CCNU); and Teniposide (VM-26).

* * * * *